US009566313B2

(12) United States Patent
Chvatchko et al.

(10) Patent No.: US 9,566,313 B2
(45) Date of Patent: *Feb. 14, 2017

(54) METHOD OF TREATING PERIPHERAL VASCULAR DISEASES USING IL-18 INHIBITORS

(75) Inventors: Yolande Chvatchko, Paris (FR); Alain Tedgui, Paris (FR); Ziad Mallat, Herbeville (FR)

(73) Assignees: MERCK SERONO SA, Vaud (CH); INSTITUT NATIONAL DE LA SANTE ET DE LA RECHERCHE MEDICALE, Paris (FR)

( * ) Notice: Subject to any disclaimer, the term of this patent is extended or adjusted under 35 U.S.C. 154(b) by 783 days.

This patent is subject to a terminal disclaimer.

(21) Appl. No.: 12/791,052

(22) Filed: Jun. 1, 2010

(65) Prior Publication Data

US 2010/0291028 A1 Nov. 18, 2010

Related U.S. Application Data

(63) Continuation of application No. 10/508,574, filed as application No. PCT/EP03/50061 on Mar. 13, 2003.

(30) Foreign Application Priority Data

Mar. 22, 2002 (EP) .................................. 02100290

(51) Int. Cl.
*A61K 38/17* (2006.01)
(52) U.S. Cl.
CPC ................................ *A61K 38/1709* (2013.01)
(58) Field of Classification Search
None
See application file for complete search history.

(56) References Cited

U.S. PATENT DOCUMENTS

| 5,877,197 A | 3/1999 | Karanewsky et al. |
| 6,605,280 B1 | 8/2003 | Novick et al. |
| 2002/0098185 A1 | 7/2002 | Sims et al. |
| 2005/0191303 A1* | 9/2005 | Torigoe et al. ............ 424/145.1 |

FOREIGN PATENT DOCUMENTS

| EP | 0974600 A2 | 1/2000 |
| EP | 1101772 A1 | 5/2001 |
| EP | 1110969 A1 | 6/2001 |
| WO | 99/09063 A1 | 2/1999 |
| WO | WO 00/12555 | * 3/2000 |
| WO | 01/85201 A2 | 11/2001 |
| WO | 01/90063 A2 | 11/2001 |
| WO | 03/080104 A3 | 10/2003 |

OTHER PUBLICATIONS

Palumbo et al. Peripheral Vascular Disease and Diabetes. Diabetes in America, 2nd ed., 1995, Chapter 17, pp. 401-408.*
Mayo Clinic website, "Gangrene". Accessed Apr. 7, 2012.*
Ross, R. The pathogenesis of atherosclerosis: a perspective for the 1990s. Nature, Apr. 29, 1993;362(6423):801-9.*
Cao et al. Interleukin-18 acts as an angiogenesis and tumor suppressor. FASEB J. 1999, 13, 2195-2202.*
Mallat et al. Interleukin-18/Interleukin-18 Binding Protein Signaling Modulates Ischemia-Induced Neovascularization in Mice Hindlimb. Circ Res. 2002;91: 441-448.*
Merck Manual, 17th ed. (Jan. 1999), pp. 168-169.
Santilli et al., Chronic critical limb ischemia: diagnosis, treatment and prognosis. Am Fam Physician., Apr. 1, 1999, 59 (7):1899-1908.
Mallat et al., Interleukin-18/interleukin-18 binding protein signaling modulates atherosclerotic lesion development and stability. Circ Res. Sep. 28, 2001, 89(7):E41-5.
Theis, F.V., Thromboangiitis obliterans: A juvenile or presenile form of atherosclerosis obliterans. Presbyterian Saint Luke S Hosp Med Bull, (1965) vol. 4, No. 1, pp. 18-26.
Gerdes, Norbert et al.; J. Exp. Med.; 195(2):245-257 (Jan. 21, 2002).
Novick, Daniela et al.; Immunity; 10:127-136 (Jan. 1999).
Numano, Fujio; International Journal of Cardiology; 75:S1-S8 (2000).
Young, James L. et al; J. Exp. Med.; 191(9):1535-1544 (May 1, 2000).

* cited by examiner

*Primary Examiner* — Dong Jiang
(74) *Attorney, Agent, or Firm* — Nixon Peabody LLP, David S. Resnick; Leena H. Karttunen Contarino; Nicole D. Kling

(57) ABSTRACT

The invention relates to the use of an inhibitor of IL-18 in the preparation of a medicament for treatment and/or prevention of peripheral vascular diseases. The invention further relates to the use of an IL-18 inhibitor for prevention of limb amputation.

6 Claims, 13 Drawing Sheets

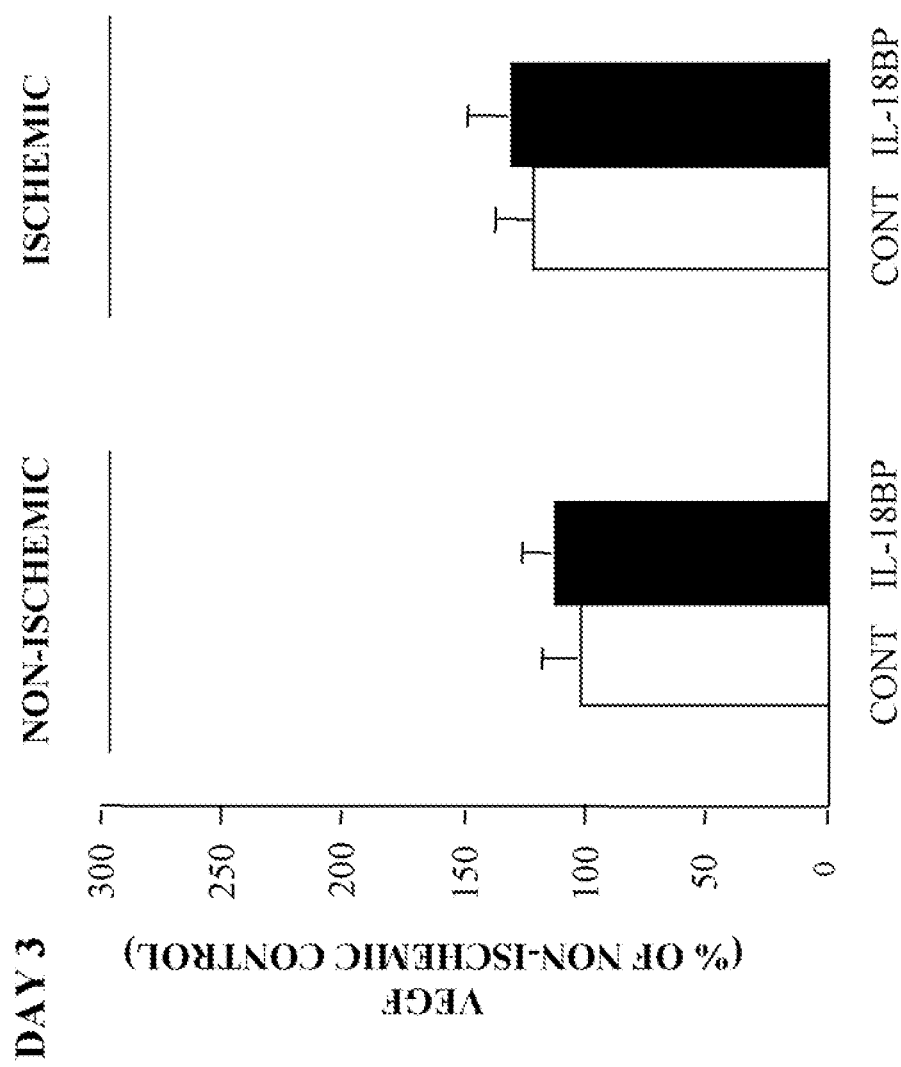

SEQUENCE LISTING

```
<160> NUMBER OF SEQ ID NOS: 5

<210> SEQ ID NO 1
<211> LENGTH: 1272
<212> TYPE: DNA
<213> ORGANISM: Homo sapiens

<400> SEQUENCE: 1
catgaactag acacctagag aagaaggatg tgacttgtag tatcctatgt ctaaattagg      60
aatatgaatc tggtttttct acaagaagtt tgagatcaca gctgactgtg ttcctgatgc     120
atccaccaaa cccagttcca tctgtgggcc tccctggctc tgtcaccagc cgttgcaccc     180
tcccaatcac aggagtcaca aacctcagac atgcagctcc tgtccacact taatatatgc     240
```

```
atgcattgga tcacccagcc ctggtctttc tgcctccatg gataactgca tgaccctgag    300
agaaaacctc cttagattta gcatcctagg ttcctcacac gcctcaccct gaatcctggc    360
cctcccgcag ccccagcgcc atttgtccca tcagtgacaa gattcatatt ctgatgtaga    420
ctctgttgcc agagccagtg ttgagccagt ccgcctcttc cccgggaagt gcctgccctt    480
ccctcctgtt agggttggct ctcgagcttg tgtgccagtt cctgggttgg ccgtgagagt    540
tctacagaca aggaggaagt gctctcggtg tatttcctgt ggtgggttca cacgcagcta    600
gacacagcta acttgagtct tggagctcct agagggaagc ttctggaaag gaaggctctt    660
caggacctct taggagccag gtaggagtct gggactacta gtgaacctag acctgtggct    720
ctggccagag ggctaggat gagagacaga gggtgtgatg gtgggtgctg ggagatgtag     780
ccgaccttgg ggctggtggc tggggagtg ggtagcctgg gaaaggccag gatgtggacg      840
gactggtatg gcattgagcc tgaagtggtc caacttgggg ttccccagtg cctaggaaag    900 ttgtccctt gaatgtcagt gtgaaggtga aggaggaagc agatgcctgt tcatatggaa      960
acaaagacct ggctgtgaag aggggaggcg acaccaaag tcctgacact gggcgggac     1020 agaattgatc tgtgagagac tcatctagtt cataccctag gtgaccctgg gggtggcatg   1080
ggggtagatt agagatccca gtctggtatc ctctggagag taggagtccc aggagctgaa   1140
ggtttctggc cactgaactt tggctaaagc agaggtgtca cagctgctca agattccctg   1200
gttaaaaagt gaaagtgaaa tagagggtcg gggcagtgct ttcccagaag gattgctcgg   1260
catcctgccc tt                                                       1272

<210> SEQ ID NO 2
<211> LENGTH: 634
<212> TYPE: DNA
<213> ORGANISM: Homo sapiens

<400> SEQUENCE: 2
gcttctggaa aggaaggctc ttcaggacct cttaggagcc aggtaggagt ctgggactac     60
tagtgaacct agacctgtgg ctctggccag aggggctagg atgagagaca gagggtgtga    120
tggtgggtgc tgggagatgt agccgacctt ggggctggtg gctggggag tgggtagcct     180 gggaaaggcc aggatgtgga cggactggta tggcattgag cctgaagtgg tccaacttgg    240
ggttccccag tgcctaggaa agttgtcccc ttgaatgtca gtgtgaaggt gaaggaggaa    300
gcagatgcct gttcatatgg aaacaaagac ctggctgtga gaggggagg cggacaccaa     360 agtcctgaca cttgggcggg acagaattga tctgtgagag actcatctag ttcataccct    420
aggtgaccct gggggtggca tgggggtaga ttagagatcc cagtctggta tcctctggag    480
agtaggagtc ccaggagctg aaggtttctg gccactgaac tttggctaaa gcagaggtgt    540
cacagctgct caagattccc tggttaaaaa gtgaaagtga atagagggt cgggggcagtg    600 cttcccagagaggattgctc ggcatcctgc cctt                                 634

<210> SEQ ID NO 3
<211> LENGTH: 122
<212> TYPE: DNA
<213> ORGANISM: Homo sapiens

<400> SEQUENCE: 3
cactgaactt tggctaaagc agaggtgtca cagctgctca agattccctg gttaaaaagt     60
gaaagtgaaa tagagggtcg gggcagtgct ttcccagaag gattgctcgg catcctgccc   120
```

```
tt                                                                        122

<210> SEQ ID NO 4
<211> LENGTH: 1061
<212> TYPE: DNA
<213> ORGANISM: Homo sapiens

<400> SEQUENCE: 4
tgcagctcct gtccacactt aatatatgca tgcattggat cacccagccc tggtctttct         60
gcctccatgg ataactgcat gaccctgaga gaaaacctcc ttagatttag catcctaggt        120
tcctcacacg cctcaccctg aatcctggcc ctcccgcagc cccagcgcca tttgtcccat        180
cagtgacaag attcatattc tgatgtagac tctgttgcca gagccagtgt tgagccagtc        240
cgcctcttcc ccgggaagtg cctgcccttc cctcctgtta gggttggctc tcgagcttgt        300
gtgccagttc ctgggttggc cgtgagagtt ctacagacaa ggaggaagtg ctctcggtgt        360
atttcctgtg gtgggttcac acgcagctag acacagctaa cttgagtctt ggagctccta        420
gagggaagct tctggaaagg aaggctcttc aggacctctt aggagccagg taggagtctg        480
ggactactag tgaacctaga cctgtggctc tggccagagg ggctaggatg agagacagag        540
ggtgtgatgg tgggtgctgg gagatgtagc cgaccttggg gctggtggct gggggagtgg        600
gtagcctggg aaaggccagg atgtggacgg actggtatgg cattgagcct gaagtggtcc        660
aacttggggt tccccagtgc ctaggaaagt tgtcccct tg aatgtcagtg tgaaggtgaa        720
ggaggaagca gatgcctgtt catatggaaa caaagacctg gctgtgaaga ggggaggcgg        780
acaccaaagt cctgacactt gggcgggaca gaattgatct gtgagagact catctagttc        840
ataccctagg tgaccctggg ggtggcatgg gggtagatta gagatcccag tctggtatcc        900
tctggagagt aggagtccca ggagctgaag gtttctggcc actgaacttt ggctaaagca        960
gaggtgtcac agctgctcaa gattccctgg ttaaaaagtg aaagtgaaat agagggtcgg       1020
ggcagtgctt tcccagaagg attgctcggc atcctgccct t                          1061

<210> SEQ ID NO 5
<211> LENGTH: 51
<212> TYPE: DNA
<213> ORGANISM: Homo sapiens

<400> SEQUENCE: 5
cccagaagca gctctggtgc tgaagagagc actgcctccc tgtgtgactg g                 51
```

METHOD OF TREATING PERIPHERAL VASCULAR DISEASES USING IL-18 INHIBITORS

CROSS-REFERENCE TO RELATED APPLICATIONS

This application is a Continuation application under 35 U.S.C. §120 of U.S. application Ser. No. 10/508,574, which is a U.S. National Phase Entry Application under 35 U.S.C. §371 of International Application PCT/EP03/50061, filed Mar. 13, 2003, which claims benefit under 35 U.S.C. 119 of the European Patent Application No. 02 100 290.2, filed Mar. 22, 2002.

FIELD OF THE INVENTION

The present invention is in the field of vascular diseases. More specifically, it relates to the use of an inhibitor of IL-18 for the treatment and/or prevention of peripheral vascular diseases. The invention further relates to the use of an IL-18 inhibitor for prevention of amputation.

BACKGROUND OF THE INVENTION

The cytokine interleukin 18 (IL-18) was initially described as an interferon-γ (IFN-γ) inducing factor (Nakamura et al., 1989). It is an early signal in the development of T-lymphocyte helper cell type 1 (TH1) responses. IL-18 acts together with IL-12, IL-2, antigens, mitogens, and possibly further factors, to induce the production of IFN-γ. IL-18 also enhances the production of GM-CSF and IL-2, potentiates anti-CD3 induced T cell proliferation, and increases Fas-mediated killing of natural killer cells.

Mature IL-18 is produced from its precursor by the IL-1β converting enzyme (ICE, caspase-1).

The IL-18 receptor consists of at least two components, IL-18R alpha and IL-18R beta, co-operating in ligand binding. High- and low-affinity binding sites for IL-18 were found in murine IL-12 stimulated T cells (Yoshimoto et al., 1998), suggesting a multiple chain receptor complex. The two receptor subunits that have been identified so far, both belonging to the IL-1 receptor family (Parnet et al., 1996; Kim et al., 2001). The signal transduction of IL-18 involves activation of NF-κB (DiDonato et al., 1997). The IL-18 receptor complex consists of two receptor chains: a ligand-binding chain termed the IL-18Rα chain and a signal-transducing chain termed the IL-18Rβ chain. The IL-18Ralpha chain was initially isolated as a cell surface protein binding to radiolabeled IL-18; the protein was purified and its amino acid sequence revealed identity with a previously reported orphan receptor termed the IL-1R-related protein (IL-1 Rrp) (Torigoe et al., 1997).

Recently, a soluble protein having a high affinity for IL-18 has been isolated from human urine, and the human and mouse cDNAs as well as the human gene were cloned (Novick et al., 1999; WO 99/09063). The protein has been designated IL-18 binding protein (IL-18BP).

IL-18BP is not the extracellular domain of one of the known IL18 receptors, but a secreted, naturally circulating protein. It belongs to a novel family of secreted proteins, further including several Poxvirus-encoded proteins (Novick et al., 1999). Urinary as well as recombinant IL-18BP specifically bind IL-18 with a high affinity and modulate the biological affinity of IL-18.

The IL-18BP gene was localized to the human chromosome 11q13, and no exon coding for a transmembrane domain was found in an 8.3 kb genomic sequence. Four splice variants or isoforms of IL-18BP generated by alternative mRNA splicing have been found in humans so far. They were designated IL-18BP a, b, c and d, all sharing the same N-terminus and differing in the C-terminus (Novick et al, 1999). These isoforms vary in their ability to bind IL-18. Of the four, hIL-18BP isoforms a and c are known to have a neutralizing capacity for IL-18. Human IL-18BP isoform binds to murine IL-18.

Peripheral vascular disorders may be arterial (occlusive or functional), venous, combined arteriovenous (e.g. arteriovenous fistula), or lymphatic. Occlusive arterial disease includes peripheral arterial occlusion and Buerger's Disease, also called thromboangiitis obliterans. Functional arterial disorders may be vasospastic (Raynaud's phenomenon and disease, acrocyanosis) or vasodilatory (erythromelalgia). They may be secondary to a local fault in the blood vessels or to disturbances in sympathetic nervous system activity, or may accompany organic vascular disease. Venous diseases include venous thrombosis and varicose veins, combined arteriovenous disorders include arteriovenous fistula, and lymphatic disorders include lymphedema and lipedema.

Peripheral arterial occlusion refers to an occlusion of blood supply to the extremities, generally by atherosclerotic plaques (atheromas), a thrombus, or an embolism.

Peripheral arterial occlusion may result in acute or chronic ischemia. Acute ischemia is caused by a ruptured proximal arteriosclerotic plaque, by acute thrombosis on preexisting atherosclerotic disease, by an embolism from the heart, aorta, or other large vessels, or a dissected aneurysm. Chronic ischemia is caused by gradual enlargement of an atheromatous plaque.

Sustained elevation of blood homocysteine, by damaging endothelial cells, predisposes to premature atherosclerosis of the aorta and its branches, the peripheral arteries, the cerebral arteries, and possibly the coronary arteries. Although homocysteine levels are usually elevated in association with other risk factors, they can be modified by diet and vitamin B supplements.

Clinical syndromes of arterial occlusion depend on the vessel involved, the extent of obstruction, how rapidly occlusion progresses, and whether collateral flow is adequate.

Acute occlusion has a history that includes sudden onset of severe pain, coldness, numbness, and pallor in an extremity. The extremity is cold and pale, and pulses are absent distal to the obstruction. Acute occlusion may cause severe ischemia manifested by sensory and motor loss and eventually (after 6 to 8 h) tender induration of muscles on palpation.

In chronic occlusion, the symptoms are related to the insidious development of tissue ischemia. The initial symptom is intermittent claudication. Symptoms of claudication are pain, ache, cramp, or tired feeling that occurs on walking. These symptoms are most common in the calf but may occur in the foot, thigh, hip, or buttocks.

Eventually, ischemic pain may occur at rest, beginning in the most distal parts of a limb as a severe, unrelenting pain aggravated by elevation and often preventing sleep.

The level of arterial occlusion and the location of intermittent claudication closely correlate, e.g. aortoiliac disease frequently causes claudication in the buttocks, hips, and calves, and the femoral pulses are reduced or absent. In femoropopliteal disease, claudication is typically in the calf, and all pulses below the femoral are absent. In patients with small vessel disease (e.g. thromboangiitis obliterans, diabetes mellitus), femoropopliteal pulses may be present but foot pulses are absent. Pallor of the involved foot after 1 to 2 min of elevation, followed by rubor on dependency, helps confirm arterial insufficiency. Venous filling time on dependency after elevation exceeds the normal limit of 15 sec. If symptoms of claudication occur with good distal pulses, spinal stenosis should be considered in the differential diagnosis.

A severely ischemic foot is painful, cold, and often numb. In chronic cases, the skin may be dry and scaly with poor nail and hair growth. As ischemia worsens, ulceration may appear (typically on the toes or heel, occasionally on the leg), especially after local trauma. Edema is usually not present unless the patient has kept the leg in a dependent position for pain relief, however, a severely ischemic leg may be atrophic. More extensive occlusion may compromise tissue viability, leading to necrosis or gangrene. Ischemia with rubor, pain, and swelling of the foot on dependency may mimic cellulitis or venous insufficiency. Arterial noninvasive tests can clarify the diagnosis.

Among the peripheral vascular diseases, Buerger's Disease (Thromboangiitis Obliterans) is an obliterative disease characterized by inflammatory changes in small and medium-sized arteries and veins.

Buerger's Disease occurs in cigarette smokers, predominantly in men aged 20 to 40. Only about 5% of cases occur in women. The frequency of diagnosis has decreased drastically in recent years because of better understanding of clinical and angiographic characteristics of this disease versus arteriosclerosis obliterans.

Although the cause is unknown, Buerger's Disease has not been documented in nonsmokers, implicating cigarette smoking as a primary etiologic factor, perhaps as a delayed type of hypersensitivity or toxic angiitis. Thromboangiitis obliterans may be a reaction to tobacco by persons with a specific phenotype, because of greater prevalence of HLA-A9 and HLA-B5 in persons with the disease; or an autoimmune disorder with cell-mediated sensitivity to types I and III human collagen, which are constituents of blood vessels.

Unlike atherosclerosis, Buerger's Disease does not involve the coronary arteries.

The disease involves small and medium-sized arteries and, frequently, superficial veins of the extremities in a segmental pattern. Rarely, in advanced disease, vessels in other parts of the body are affected. The pathologic appearance is that of a nonsuppurative panarteritis or panphlebitis with thrombosis of involved vessels. Proliferation of endothelial cells and infiltration of the intimal layer with lymphocytes occur in the acute lesion, but the internal elastic lamina is intact. The thrombus becomes organized and later incompletely recanalizes. The media is well preserved but may be infiltrated with fibroblasts. Because the adventitia usually is more extensively infiltrated with fibroblasts, older lesions show periarterial fibrosis, which may also involve the adjacent vein and nerve.

The symptoms and signs are those of arterial ischemia and of superficial thrombophlebitis. Onset is gradual, starting in the most distal vessels of the upper and lower extremities and progressing proximally, culminating in distal gangrene. The patient may complain of coldness, numbness, tingling, or burning before there is objective evidence of disease. Raynaud's phenomenon is common. Intermittent claudication occurs in the involved extremity (usually the arch of the foot or the leg, but rarely the hand, arm, or thigh). Pain is persistent with more severe ischemia, e.g. in the pregangrenous stage and with ulceration or gangrene. Frequently, sympathetic nerve overactivity is manifested by coldness, excessive sweating, and cyanosis of the involved extremity, probably caused by the severe, persistent pain.

Ischemic ulceration and gangrene, usually of one or more digits, may occur early in the disease but not acutely. Noninvasive studies show severe decreases in blood flow and pressure in affected toes, feet, and fingers. The disease progresses proximally.

Another peripheral vascular disease is peripheral arterial disease, in which patients with lower extremity peripheral arterial disease (PAD) may progress to severe, limb-threatening ischemia. Ischemic rest pain, nonhealing ulcerations, and gangrene are all harbingers of poor outcomes. These patients are at high risk of limb loss. Prompt detection and evaluation of severe limb ischemia followed by efficient revascularization are required for limb salvage and preservation of overall health.

Chronic critical limb ischemia is the end result of arterial occlusive disease, most commonly atherosclerosis. In addition to atherosclerosis in association with hypertension, hypercholesterolemia, cigarette smoking and diabetes less frequent causes of chronic critical limb ischemia include Buerger's disease, or thromboangiitis obliterans, and some forms of arteritis.

The development of chronic critical limb ischemia usually requires multiple sites of arterial obstruction that severely reduce blood flow to the tissues. Critical tissue ischemia is manifested clinically as rest pain, non-healing wounds (because of the increased metabolic requirements of wound healing) or tissue necrosis (gangrene).

Ischemic rest pain is classically described as a burning pain in the ball of the foot and toes that is worse at night when the patient is in bed. Ischemic rest pain is located in the foot, where tissue is farthest from the heart and distal to the arterial occlusions. Non-healing wounds are usually found in areas of foot trauma caused by improperly fitting shoes or an injury. A wound is generally considered to be nonhealing if it fails to respond to a four- to 12-week trial of conservative therapy such as regular dressing changes, avoidance of trauma, treatment of infection and debridement of necrotic tissue.

Gangrene is usually found on the toes. It develops when the blood supply is so low that spontaneous necrosis occurs in the most poorly perfused tissues.

While carefully designed conservative therapy can benefit many patients with critical limb ischemia, the severe nature of their disease may lead to consideration of operative intervention. Surgical interventions include revascularization or amputation. If the patient wants to undergo revascularization and is an acceptable operative candidate, arteriography is often performed for further evaluation and planning of revascularization. At some centers, magnetic resonance angiography is used as an alternative or supplement to arteriography to minimize the risk of dye exposure. Limb preservation by means of revascularization is cost-effective, leads to a better quality of life for most patients and is associated with lower perioperative morbidity and mortality than amputation. Limb preservation should be the goal in most patients with chronic critical limb ischemia.

The feasibility of revascularization is determined by the arteriographic findings as well as the availability of a bypass conduit. Angioplasty or stent placement, or both, is most successful with short, proximal lesions, such as those in patients with claudication, but is unlikely to be the only treatment necessary in the setting of critical limb ischemia because of the multilevel nature of the arterial occlusive disease. The ideal bypass conduit is the greater saphenous vein, but other conduits include the lesser saphenous veins, the arm veins or a prosthetic conduit. In most surgical series, three-year bypass patency rates of calf arteries range from 40 percent for prosthetic bypasses to 85 percent for saphenous vein bypasses. In comparison, studies of conservative therapy have demonstrated a 25 to 49 percent success rate with nonhealing wounds and a 50 to 80 percent rate of improvement in ischemic rest pain.

Primary amputation may be indicated in certain patients, such as those with extensive tissue necrosis, life-threatening infection or lesions not amenable to revascularization. The decision to monitor the patient's condition with watchful waiting and conservative management or to perform revascularization or amputation depends on careful assessment of the attendant risks and benefits of surgery versus conservative management.

More importantly, it depends on the patient's interpretation of the invasiveness or appropriateness of the available options. Even patients unable to walk because of their condition may consider amputation inappropriate, and not all patients are motivated to do the work necessary for rehabilitation after amputation. If the decision is made to amputate, the level of amputation should be one that has the greatest likelihood of healing while giving the patient the maximal chance for functional rehabilitation.

Diagnosis of chronic critical limb ischemia involves manifested pain at rest, non-healing wounds and gangrene. Ischemic rest pain is typically described as a burning pain in the arch or distal foot that occurs while the patient is recumbent but is relieved when the patient returns to a position in which the feet are dependent. Objective hemodynamic parameters that support the diagnosis of critical limb ischemia include an ankle-brachial index of 0.4 or less, an ankle systolic pressure of 50 mm Hg or less, or a toe systolic pressure of 30 mm Hg or less. Intervention may include conservative therapy, revascularization or amputation. Progressive gangrene, rapidly enlarging wounds or continuous ischemic rest pain can signify a threat to the limb and suggest the need for revascularization in patients without prohibitive operative risks. Bypass grafts are usually required because of the multilevel and distal nature of the arterial narrowing in critical limb ischemia. Patients with diabetes are more likely than other patients to have distal disease that is less amenable to bypass grafting. Compared with amputation, revascularization is more cost-effective and is associated with better perioperative morbidity and mortality. Limb preservation should be the goal in most patients with critical limb ischemia.

At present, the major treatment of peripheral vascular diseases include invasive treatment such as angioplasty of even limb amputation. Identification of drugs that stimulate peripheral neovascularization without increasing atherosclerotic plaque progression is of major therapeutic importance in this medical field.

SUMMARY OF THE INVENTION

The invention is based on the finding that an inhibitor of IL-18 stimulates neovascularization after induction of peripheral ischemia in an experimental animal model. Neovascularization occurred in association with an activation of VEGF/Akt signaling and was accompanied by an increase in bone marrow endothelial progenitor cell mobilization and differentiation.

On the basis of these results, new therapeutic approaches for treating or preventing peripheral vascular diseases requiring neo- or revascularization are provided.

The invention therefore relates to the use of an IL-18 inhibitor for treatment and/or prevention of peripheral vascular diseases, in particular of peripheral ischemia.

The invention further relates to the use of an IL-18 inhibitor for the manufacture of a medicament for the treatment and/or prevention of claudication and gangrene.

Furthermore, the invention relates to the use of an IL-18 inhibitor for the manufacture of a medicament for the prevention of amputation, in particular limb amputation.

The use of an expression vector comprising the coding sequence of an inhibitor of IL-18, as well as the use of an expression vector for inducing and/or enhancing the endogenous production of an inhibitor of IL-18 in a cell, for treatment or prevention of peripheral vascular diseases is also within the present invention.

The invention further relates to a method of treatment of peripheral vascular diseases comprising administering to a host in need thereof an effective inhibiting amount of an IL-18 inhibitor.

BRIEF DESCRIPTION OF THE DRAWINGS

FIGS. 3A-3C show A) Representative western-blot of VEGF protein content in the non-ischemic and ischemic leg, 28 days after femoral artery occlusion. B) and C) Quantitative evaluation of VEGF protein levels expressed as a ratio of protein content in ischemic limb to that in non-ischemic one. Values are mean±SEM, n=7 per group. **$p<0.01$ versus non-ischemic control and †$p<0.05$ versus ischemic control.

DETAILED DESCRIPTION OF THE INVENTION

Figure 1A:
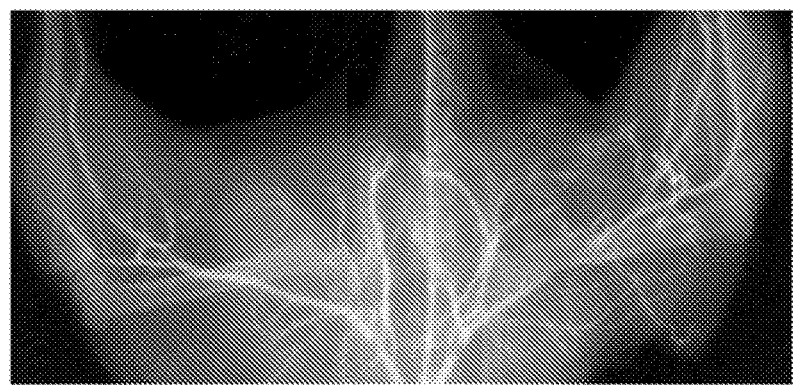
FIG. 1: shows A) Representative microangiography of the right ischemic and left non-ischemic hindlimbs, 3 and 28 days after femoral artery occlusion in the mouse. B) shows the ischemic/non-ischemic angiographic score in mice treated with pcDNA3-mIL18BP (IL-18BP) or empty plasmid (Control) for 3 or 28 days. Values are mean±SEM, n=7 per group. **$p<0.01$ versus control mice.

The present invention is based on the finding that IL-18 inhibitors significantly increase post-ischemic angiogenesis after limb ischemia without affecting vessel density of the non-ischemic limb in an in vivo murine disease model. Therefore, the invention provides for a new therapeutic approach to treating or preventing peripheral vascular diseases requiring enhanced tissue perfusion.

The invention therefore relates to the use of an IL-18 inhibitor for the manufacture of a medicament for the treatment and/or prevention of a peripheral vascular disease.

The term "prevention" within the context of this invention refers not only to a complete prevention of a certain effect, but also to any partial or substantial prevention, attenuation, reduction, decrease or diminishing of the effect before or at early onset of disease.

The term "treatment" within the context of this invention refers to any beneficial effect on progression of disease, including attenuation, reduction, decrease or diminishing of the pathological development after onset of disease.

The term "peripheral vascular disease" as used herein refers to diseases or disorders affecting the arteries, veins, and lymphatics of the extremities. Peripheral vascular disorders may be arterial (occlusive or functional), venous, combined arteriovenous (e.g., arteriovenous fistula), or lymphatic. Occlusive arterial disease includes peripheral arterial occlusion and thromboangiitis obliterans. Functional arterial disorders may be vasospastic (Raynaud's phenomenon and disease, acrocyanosis) or vasodilatory (erythromelalgia). They may also be secondary to a local fault in the blood vessels, or to disturbances in sympathetic nervous system activity, or they may accompany organic vascular disease. Venous diseases include venous thrombosis and varicose veins, combined arteriovenous disorders include arteriovenous fistula, and lymphatic disorders include lymphedema and lipedema.

The term peripheral vascular disease is meant to encompass all medical indications, diseases, disorders or symptoms described in the "Background of the Invention" above.

The term "inhibitor of IL-18" within the context of this invention refers to any molecule modulating IL-18 production and/or action in such a way that IL-18 production and/or action is attenuated, reduced, or partially, substantially or completely prevented or blocked.

An inhibitor of production can be any molecule negatively affecting the synthesis, processing or maturation of IL-18. The inhibitors considered according to the invention can be, for example, suppressors of gene expression of the interleukin IL-18, antisense mRNAs reducing or preventing the transcription of the IL-18 mRNA or leading to degradation of the mRNA, proteins impairing correct folding, or partially or substantially preventing secretion of IL-18, proteases degrading IL-18, once it has been synthesized, inhibitors of proteases cleaving pro-IL-18 in order to generate mature IL-18, such as inhibitors of caspase-1, and the like.

An inhibitor of IL-18 action can be an IL-18 antagonist, for example. Antagonists can either bind to or sequester the IL-18 molecule itself with sufficient affinity and specificity to partially or substantially neutralize the IL-18 or IL-18 binding site(s) responsible for IL-18 binding to its ligands (like, e.g. to its receptors). An antagonist may also inhibit the IL-18 signaling pathway, which is activated within the cells upon binding of IL-18 to its receptor binding.

Inhibitors of IL-18 action may also be soluble IL-18 receptors or molecules mimicking the receptors, or agents blocking the IL-18 receptors, or IL-18 antibodies, such as polyclonal or monoclonal antibodies, or any other agent or molecule preventing the binding of IL-18 to its targets, thus diminishing or preventing triggering of the intra- or extracellular reactions mediated by IL-18.

In a preferred embodiment of the invention, the peripheral vascular disease is peripheral arterial disease.

"Peripheral arterial disease" is a disorder involving narrowing of the arteries anywhere from the arms to the aorta and the arteries of the legs. The onset can be sudden or gradual and generally results in ischemia (decreased delivery of oxygen to the area the vessel supplies).

Preferably, in accordance with the present invention, the peripheral arterial disease concerns the lower extremities. Peripheral arterial disease or occlusion may be chronic or acute. Peripheral arterial disease is frequently associated with claudication.

Therefore, the present invention further relates to the use of an IL-18 inhibitor for treatment and/or prevention of claudication. Claudication is pain in the leg, in particular in the calf, that comes and goes to cause limping. Claudication typically is felt while walking, and subsides with rest. It is, therefore, commonly referred to as intermittent claudication. The usually intermittent nature of the pain of claudication is due to a temporary inadequate supply of oxygen to the muscles of the leg. The poor oxygen supply is a result of narrowing or occlusion of the arteries that supply the leg with blood. This limits the supply of oxygen to the leg muscles and is felt especially when the oxygen requirement of these muscles rises with exercise or walking.

In a preferred embodiment of the invention, the peripheral vascular disease is Thromboangiitis Obliterans (Buerger's Disease). "Buerger's Disease" is an obliterative disease characterized by inflammatory changes in small and medium-sized arteries and veins which often occurs in cigarette smokers, predominantly in men aged 20 to 40.

The disease involves small and medium-sized arteries and, frequently, superficial veins of the extremities in a segmental pattern.

In a further preferred embodiment, the peripheral vascular disease is peripheral ischemia, in particular limb ischemia. "Ischemia" is a deficiency in blood supply, generally due to occlusion or trauma of blood vessels. "Peripheral ischemia" particularly refers to ischemia in the limbs, i.e. the arms or legs, leading to a deficiency in oxygen supply of the corresponding limb tissue.

In yet a further embodiment of the present invention, the limb ischemia is critical limb ischemia. "Critical limb ischaemia" is a state in which the blood supply to the limb is so poor as to threaten its survival. The presence of rest pain, ulceration or gangrene indicates critical limb ischaemia. Gangrene is the term used to describe dead tissue, and it often occurs as a result of or in combination with limb ischemia. An ischaemic ulcer is caused by an inadequate blood supply.

Critical limb ischemia, including ganrene or ulcers, require revascularization in order to prevent amputation of the limb. Therefore, the present invention also relates to the use of IL-18 inhibitors for treatment and/or prevention of gangrene and ulcers.

The ultimate consequence of peripheral vascular disease, and in particular of peripheral ischemia, may be amputation of the affected limb, in particular the affected lower limb or foot. Revascularization will lead to reperfusion of the affected tissue and thus helps the healing process.

Therefore, the invention further relates to the use of an IL-18 inhibitor for the manufacture of a medicament for the prevention of amputation of the limbs, in particular of a lower limb, foot or toe(s).

In a preferred embodiment of the present invention, the inhibitor of IL-18 is selected from inhibitors of caspase-1 (ICE), antibodies directed against IL-18, antibodies directed against any of the IL-18 receptor subunits, inhibitors of the IL-18 signaling pathway, antagonists of IL-18 which compete with IL-18 and block the IL-18 receptor, and IL-18 binding proteins, isoforms, muteins, fused proteins, functional derivatives, active fractions or circularly permutated derivatives thereof inhibiting the biological activity of IL-18.

The term "IL-18 binding proteins" is used herein synonymously with "IL-18 binding protein" or "IL18BP". It comprises IL-18 binding proteins as defined in WO 99/09063 or in Novick et al., 1999, including splice variants and/or isoforms of IL-18 binding proteins, as defined in Kim et al., 2000, which bind to IL-18. In particular, human isoforms a and c of IL-18BP are useful in accordance with the presence invention. The proteins useful according to the present invention may be glycosylated or non-glycosylated, they may be derived from natural sources, such as urine, or they may preferably be produced recombinantly. Recombinant expression may be carried out in prokaryotic expression systems like *E. coli*, or in eukaryotic, and preferably in mammalian, expression systems. A cell line that is particularly well suited for expression of mammalian proteins is the Chinese Hamster Ovary (CHO) cell line.

As used herein the term "muteins" refers to analogs of an IL-18BP, or analogs of a viral IL-18BP, in which one or more of the amino acid residues of a natural IL-18BP or viral IL-18BP are replaced by different amino acid residues, or are deleted, or one or more amino acid residues are added to the natural sequence of an IL-18BP, or a viral IL-18BP, without changing considerably the activity of the resulting products as compared with the wild type IL-18BP or viral IL-18BP. These muteins are prepared by known synthesis and/or by site-directed mutagenesis techniques, or any other known technique suitable therefor.

Muteins in accordance with the present invention include proteins encoded by a nucleic acid, such as DNA or RNA, which hybridizes to DNA or RNA, which encodes an IL-18BP or encodes a viral IL-18BP, as described in WO 99/09063, under stringent conditions. The term "stringent conditions" refers to hybridization and subsequent washing conditions, which those of ordinary skill in the art conventionally refer to as "stringent". See Ausubel et al., Current Protocols in Molecular Biology, supra, Interscience, N.Y., §§6.3 and 6.4 (1987, 1992), and Sambrook et al., supra. Without limitation, examples of stringent conditions include washing conditions 12-20° C. below the calculated Tm of the hybrid under study in, e.g., 2×SSC and 0.5% SDS for 5 minutes, 2×SSC and 0.1% SDS for 15 minutes; 0.1×SSC and 0.5% SDS at 37° C. for 30-60 minutes and then, a 0.1×SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC. See Ausubel, supra.

Any such mutein preferably has a sequence of amino acids sufficiently duplicative of that of an IL-18BP, or sufficiently duplicative of a viral IL-18BP, such as to have an activity comparable to IL-18BP. One activity of IL-18BP is its capability of binding IL-18. As long as the mutein has substantial binding activity to IL-18, it can be used in the purification of IL-18, such as by means of affinity chromatography, and thus can be considered to have substantially similar activity to IL-18BP. Thus, it can be determined whether any given mutein has substantially the same activity as IL-18BP by means of routine experimentation comprising subjecting such a mutein, e.g., to a simple sandwich competition assay to determine whether or not it binds to an appropriately labeled IL-18, such as radioimmunoassay or ELISA assay.

In a preferred embodiment, any such mutein has at least 40% identity or homology with the sequence of either an IL-18BP or a virally-encoded IL-18BP homologue, as defined in WO 99/09063. More preferably, it has at least 50%, at least 60%, at least 70%, at least 80% or, most preferably, at least 90% identity or homology thereto.

Muteins of IL-18BP polypeptides or muteins of viral IL-18BPs, which can be used in accordance with the present invention, or nucleic acid coding therefor, include a finite set of substantially corresponding sequences as substitution peptides or polynucleotides which can be routinely obtained by one of ordinary skill in the art, without undue experimentation, based on the teachings and guidance presented herein.

Preferred changes for muteins in accordance with the present invention are what are known as "conservative" substitutions. Conservative amino acid substitutions of IL-18BP polypeptides or proteins or viral IL-18BPs, may include synonymous amino acids within a group which have sufficiently similar physicochemical properties that substitution between members of the group will preserve the biological function of the molecule (Grantham, 1974). It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues. Proteins and muteins produced by such deletions and/or insertions come within the purview of the present invention.

Preferably, the synonymous amino acid groups are those defined in Table 1. More preferably, the synonymous amino acid groups are those defined in Table 2; and most preferably the synonymous amino acid groups are those defined in Table 3.

TABLE 1

Preferred Groups of Synonymous Amino Acids

| Amino Acid | Synonymous Group |
| --- | --- |
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE 2

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE 3

Most Preferred Groups of Synonymous Amino Acids

| Amino Acid | Synonymous Group |
|---|---|
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining muteins of IL-18BP polypeptides or proteins, or muteins of viral IL-18BPs, for use in the present invention include any known method steps, such as presented in U.S. Pat. Nos. 4,959,314, 4,588,585 and 4,737,462, to Mark et al; U.S. Pat. No. 5,116,943 to Koths et al., U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 (Shaw et al).

The term "fused protein" refers to a polypeptide comprising an IL-18BP, or a viral IL-18BP, or a mutein or fragment thereof, fused with another protein, which, e.g., has an extended residence time in body fluids. An IL-18BP or a viral IL-18BP, may thus be fused to another protein, polypeptide or the like, e.g., an immunoglobulin or a fragment thereof.

"Functional derivatives" as used herein cover derivatives of IL-18BPs or a viral IL-18BP, and their muteins and fused proteins, which may be prepared from the functional groups which occur as side chains on the residues or the N- or C-terminal groups, by means known in the art, and are included in the invention as long as they remain pharmaceutically acceptable, i.e. they do not destroy the activity of the protein which is substantially similar to the activity of IL-18BP, or viral IL-18BPs, and do not confer toxic properties on compositions containing it.

These derivatives may, for example, include polyethylene glycol side-chains, which may mask antigenic sites and extend the residence of an IL-18BP or a viral IL-18BP in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl or threonyl residues) formed with acyl moieties.

As "active fractions" of an IL-18BP, or a viral IL-18BP, muteins and fused proteins, the present invention covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction has substantially similar activity to IL-18BP.

In a further preferred embodiment of the invention, the inhibitor of IL-18 is antibody directed against IL-18 or its receptor, the IL-18R. Antibodies directed to any of the IL-18R subunits, called IL-18Rα and β, may be used in accordance with the present invention.

The antibodies according to the invention may be polyclonal or monoclonal, chimeric, humanized, or even fully human. Recombinant antibodies and fragments thereof are characterized by high affinity binding to IL-18 or IL-18R in vivo and low toxicity. The antibodies which can be used in the invention are characterized by their ability to treat patients for a period sufficient to have good to excellent regression or alleviation of the pathogenic condition or any symptom or group of symptoms related to a pathogenic condition, and a low toxicity.

Neutralizing antibodies are readily raised in animals such as rabbits, goat or mice by immunization with IL-18 or IL-18Rα or β. Immunized mice are particularly useful for providing sources of B cells for the manufacture of hybridomas, which in turn are cultured to produce large quantities of anti-IL-18 monoclonal antibodies.

Chimeric antibodies are immunoglobulin molecules characterized by two or more segments or portions derived from different animal species. Generally, the variable region of the chimeric antibody is derived from a non-human mammalian antibody, such as murine monoclonal antibody, and the immunoglobulin constant region is derived from a human immunoglobulin molecule. Preferably, both regions and the combination have low immunogenicity as routinely determined (Elliott et al., 1994). Humanized antibodies are immunoglobulin molecules created by genetic engineering techniques in which the murine constant regions are replaced with human counterparts while retaining the murine antigen binding regions. The resulting mouse-human chimeric antibody preferably have reduced immunogenicity and improved pharmacokinetics in humans (Knight et al., 1993).

Thus, in a further preferred embodiment, IL-18 or IL-18R antibody is a humanized antibody. Preferred examples of humanized anti-IL-18 antibodies are described in the European Patent Application EP 0 974 600, for example.

In yet a further preferred embodiment, the antibody is fully human. The technology for producing human antibodies is described in detail e.g. in WO00/76310, WO99/53049, U.S. Pat. No. 6,162,963 or AU5336100.

One method for the preparation of fully human antibodies consist of "humanization" of the mouse humoral immune system, i.e. production of mouse strains able to produce human Ig (Xenomice), by the introduction of human immunoglobulin (Ig) loci into mice in which the endogenous Ig genes have been inactivated. The Ig loci are complex in terms of both their physical structure and the gene rearrangement and expression processes required to ultimately produce a broad immune response. Antibody diversity is primarily generated by combinatorial rearrangement between different V, D, and J genes present in the Ig loci. These loci also contain the interspersed regulatory elements, which control antibody expression, allelic exclusion, class switching and affinity maturation. Introduction of un-rearranged human Ig transgenes into mice has demonstrated that the mouse recombination machinery is compatible with human genes. Furthermore, hybridomas secreting antigen specific hu-mAbs of various isotypes can be obtained by Xenomice immunisation with antigen.

Fully human antibodies and methods for their production are known in the art (Mendez et at (1997); Buggemann et at (1991); Tomizuka et al., (2000) Patent WO 98/24893).

In a highly preferred embodiment of the present invention, the inhibitor of IL-18 is an IL-18BP, or an isoform, a mutein, fused protein, functional derivative, active fraction or circularly permutated derivative thereof. These isoforms, muteins, fused proteins or functional derivatives retain the biological activity of IL-18BP, in particular the binding to IL-18, and preferably have essentially at least an activity similar to IL-18BP. Ideally, such proteins have an enhanced biological activity as compared to unmodified IL-18BP. Preferred active fractions have an activity which is better than the activity of IL-18BP, or which have further advantages, like a better stability or a lower toxicity or immunogenicity, or they are easier to produce in large quantities, or easier to purify.

The sequences of IL-18BP and its splice variants/isoforms can be taken from WO99/09063 or from Novick et al., 1999, as well as from Kim et al., 2000.

Functional derivatives of IL-18BP may be conjugated to polymers in order to improve the properties of the protein, such as the stability, half-life, bioavailability, tolerance by the human body, or immunogenicity. To achieve this goal, IL18-BP may be linked e.g. to Polyethlyenglycol (PEG). PEGylation may be carried out by known methods, described in WO 92/13095, for example.

Therefore, in a preferred embodiment of the present invention, the inhibitors of IL-18, and in particular the IL-18BP is PEGylated.

In a further preferred embodiment of the invention, the inhibitor of IL-18 comprises an immunoglobulin fusion, i.e. the inhibitor of IL-18 is a fused protein comprising all or part of an IL-18 binding protein, which is fused to all or a portion of an immunoglobulin. Methods for making immunoglobulin fusion proteins are well known in the art, such as the ones described in WO 01/03737, for example. The person skilled in the art will understand that the resulting fusion protein of the invention retains the biological activity of IL-18BP, in particular the binding to IL-18. The fusion may be direct, or via a short linker peptide which can be as short as 1 to 3 amino acid residues in length or longer, for example, 13 to 20 amino acid residues in length. Said linker may be a tripeptide of the sequence E-F-M (Glu-Phe-Met), for example, or a 13-amino acid linker sequence comprising Glu-Phe-Gly-Ala-Gly-Leu-Val-Leu-Gly-Gly-Gln-Phe-Met introduced between the IL-18BP sequence and the immunoglobulin sequence. The resulting fusion protein has improved properties, such as an extended residence time in body fluids (half-life), increased specific activity, increased expression level, or the purification of the fusion protein is facilitated.

In a preferred embodiment, IL-18BP is fused to the constant region of an Ig molecule. Preferably, it is fused to heavy chain regions, like the CH2 and CH3 domains of human IgG1 or IgG2, for example. The generation of specific fusion proteins comprising IL-18BP and a portion of an immunoglobulin are described in example 11 of WO 99/09063, for example. Other isoforms of Ig molecules are also suitable for the generation of fusion proteins according to the present invention, such as isoforms $IgG_2$ or $IgG_4$, or other Ig classes, like IgM or IgA, for example. Fusion proteins may be monomeric or multimeric, hetero- or homo-multimeric.

In yet a further embodiment of the invention, an inhibitor of IL-18 is used in combination with one or more other molecules active in the clinical conditions of the invention, such as vasodilators, Ca-blockers, aspirin, beta-blockers or the like. TNF antagonists may also be used in combination with an IL-18 inhibitor in accordance with the present invention, for example. TNF antagonists exert their activity in several ways. First, antagonists can bind to or sequester the TNF molecule itself with sufficient affinity and specificity to partially or substantially neutralize the TNF epitope or epitopes responsible for TNF receptor binding (hereinafter termed "sequestering antagonists"). A sequestering antagonist may be, for example, an antibody directed against TNF.

Alternatively, TNF antagonists can inhibit the TNF signaling pathway activated by the cell surface receptor after TNF binding (hereinafter termed "signaling antagonists"). Both groups of antagonists are useful, either alone or together, in combination with an IL-18 inhibitor, in the therapy or prevention of peripheral vascular disease.

TNF antagonists are easily identified and evaluated by routine screening of candidates for their effect on the activity of native TNF on susceptible cell lines in vitro, for example human B cells, in which TNF causes proliferation and immunoglobulin secretion. The assay contains TNF formulation at varying dilutions of candidate antagonist, e.g. from 0.1 to 100 times the molar amount of TNF used in the assay, and controls with no TNF or only antagonist (Tucci et al., 1992).

Sequestering antagonists are the preferred TNF antagonists to be used according to the present invention. Amongst sequestering antagonists, those polypeptides that bind TNF with high affinity and possess low immunogenicity are preferred. Soluble TNF receptor molecules and neutralizing antibodies to TNF are particularly preferred. For example, soluble TNF-RI and TNF-RII are useful in the present invention. Truncated forms of these receptors, comprising the extracellular domains of the receptors or functional portions thereof, are more particularly preferred antagonists according to the present invention. Truncated soluble TNF type-I and type-II receptors are described in EP914431, for example.

Truncated forms of the TNF receptors are soluble and have been detected in urine and serum as 30 kDa and 40 kDa TNF inhibitory binding proteins, which are called TBPI and TBPII, respectively (Engelmann et al., 1990). The simultaneous, sequential, or separate use of the IL-18 inhibitor with the TNF antagonist is preferred according to the invention.

In a further preferred embodiment, human soluble TNF-RI (TBPI) is the TNF antagonist to be used according to the invention. The natural and recombinant soluble TNF receptor molecules and methods of their production have been described in the European Patents EP 308 378, EP 398 327 and EP 433 900.

Derivatives, fragments, regions and biologically active portions of the receptor molecules functionally resemble the receptor molecules that can also be used in the present invention. Such biologically active equivalent or derivative of the receptor molecule refers to the portion of the polypeptide, or of the sequence encoding the receptor molecule, that is of sufficient size and able to bind TNF with such an affinity that the interaction with the membrane-bound TNF receptor is inhibited or blocked.

The IL-18 inhibitor can be used simultaneously, sequentially or separately with the TNF inhibitor.

In a further preferred embodiment of the present invention, the inhibitor of IL-18 is used in an amount of about 0.01 to 100 mg/kg or about 1 to 10 mg/kg or 2 to 5 mg/kg.

The IL-18 inhibitor according to the invention is preferably administered systemically, and preferably subcutaneously or intramuscularly. It may be administered daily, or every other day. Sustained release formulations make it possible to administer less often, such as once a week, for instance.

The invention further relates to the use of an expression vector comprising the coding sequence of an inhibitor of IL-18 in the preparation of a medicament for the prevention and/or treatment of a peripheral vascular disease. Thus, a gene therapy approach is considered in order to deliver the IL-18 inhibitor to the site where it is required. In order to treat and/or prevent a peripheral vascular disease, the gene therapy vector comprising the sequence of an inhibitor of IL-18 may be injected directly into the diseased tissue, for example, thus avoiding problems involved in systemic administration of gene therapy vectors, like dilution of the vectors, reaching and targeting of the target cells or tissues, and of side effects.

The use of a vector for inducing and/or enhancing the endogenous production of an inhibitor of IL-18 in a cell normally silent for expression of an IL-18 inhibitor, or which expresses amounts of the inhibitor which are not sufficient, are also contemplated according to the invention. The vector may comprise regulatory sequences functional in the cells desired to express the inhibitor or IL-18. Such regulatory sequences may be promoters or enhancers, for example. The regulatory sequence may then be introduced into the right locus of the genome by homologous recombination, thus operably linking the regulatory sequence with the gene, the expression of which is required to be induced or enhanced. The technology is usually referred to as "Endogenous Gene Activation" (EGA), and it is described e.g. in WO 91/09955.

It will be understood by the person skilled in the art that it is also possible to shut down IL-18 expression directly, without using an inhibitor of IL-18, with the same technique. To do that, a negative regulation element, like e.g. a silencing element, may be introduced into the gene locus of IL-18, thus leading to down-regulation or prevention of IL-18 expression. The person skilled in the art will understand that such down-regulation or silencing of IL-18 expression has the same effect as the use of an IL-18 inhibitor in order to prevent and/or treat disease.

The invention further relates to the use of a cell that has been genetically modified to produce an inhibitor of IL-18 in the manufacture of a medicament for the treatment and/or prevention of a peripheral vascular disease.

The IL-18 inhibitor to be used in accordance with the present invention may be preferable administered as a pharmaceutical composition, optionally in combination with a therapeutically effective amount of a TNF inhibitor or another drug active in treatment or prevention of a peripheral vascular disease.

IL-18BP and its isoforms, muteins, fused proteins, functional derivatives, active fractions or circularly permutated derivatives as described above are the preferred active ingredients of the pharmaceutical compositions.

The definition of "pharmaceutically acceptable" is meant to encompass any carrier, which does not interfere with effectiveness of the biological activity of the active ingredient and that is not toxic to the host to which it is administered. For example, for parenteral administration, the active protein(s) may be formulated in a unit dosage form for injection in vehicles such as saline, dextrose solution, serum albumin and Ringer's solution.

The active ingredients of the pharmaceutical composition according to the invention can be administered to an individual in a variety of ways. The routes of administration include intradermal, transdermal (e.g. in slow release formulations), intramuscular, intraperitoneal, intravenous, subcutaneous, oral, intracranial, epidural, topical, and intranasal routes. Any other therapeutically efficacious route of administration can be used, for example absorption through epithelial or endothelial tissues or by gene therapy wherein a DNA molecule encoding the active agent is administered to the patient (e.g. via a vector), which causes the active agent to be expressed and secreted in vivo. In addition, the protein(s) according to the invention can be administered together with other components of biologically active agents such as pharmaceutically acceptable surfactants, excipients, carriers, diluents and vehicles.

For parenteral (e.g. intravenous, subcutaneous, intramuscular) administration, the active protein(s) can be formulated as a solution, suspension, emulsion or lyophilized powder in association with a pharmaceutically acceptable parenteral vehicle (e.g. water, saline, dextrose solution) and additives that maintain isotonicity (e.g. mannitol) or chemical stability (e.g. preservatives and buffers). The formulation is sterilized by commonly used techniques.

The bioavailability of the active protein(s) according to the invention can also be ameliorated by using conjugation procedures which increase the half-life of the molecule in the human body, for example linking the molecule to polyethylenglycol, as described in the PCT Patent Application WO 92/13095.

The therapeutically effective amounts of the active protein(s) will be a function of many variables, including the type of antagonist, the affinity of the antagonist for IL-18, any residual cytotoxic activity exhibited by the antagonists, the route of administration, the clinical condition of the patient (including the desirability of maintaining a non-toxic level of endogenous IL-18 activity).

A "therapeutically effective amount" is such that when administered, the IL-18 inhibitor results in inhibition of the biological activity of IL-18. The dosage administered, as single or multiple doses, to an individual will vary depending upon a variety of factors, including IL-18 inhibitor pharmacokinetic properties, the route of administration, patient conditions and characteristics (sex, age, body weight, health, size), extent of symptoms, concurrent treatments, frequency of treatment and the effect desired. Adjustment and manipulation of established dosage ranges are well within the ability of those skilled in the art, as well as in vitro and in vivo methods of determining the inhibition of IL-18 in an individual.

According to the invention, the inhibitor of IL-18 is used in an amount of about 0.001 to 100 mg/kg or about 0.01 to 10 mg/kg or body weight, or about 0.1 to 5 mg/kg of body weight or about 1 to 3 mg/kg of body weight or about 2 mg/kg of body weight.

The route of administration which is preferred according to the invention is administration by subcutaneous route. Intramuscular administration is further preferred according to the invention. In order to administer the IL-18 inhibitor directly to the place of its action, it is also preferred to administer it topically.

In further preferred embodiments, the inhibitor of IL-18 is administered daily or every other day.

The daily doses are usually given in divided doses or in sustained release form effective to obtain the desired results. Second or subsequent administrations can be performed at a dosage which is the same, less than or greater than the initial or previous dose administered to the individual. A second or subsequent administration can be administered during or prior to onset of the disease.

According to the invention, the IL-18 inhibitor can be administered prophylactically or therapeutically to an individual prior to, simultaneously or sequentially with other therapeutic regimens or agents (e.g. multiple drug regimens), in a therapeutically effective amount, in particular with a TNF inhibitor and/or another vascularprotective agent. Active agents that are administered simultaneously with other therapeutic agents can be administered in the same or different compositions.

The invention further relates to a method for the preparation of a pharmaceutical composition comprising admixing an effective amount of an IL-18 inhibitor and/or a TNF antagonist with a pharmaceutically acceptable carrier.

The invention further relates to a method of treatment of a peripheral vascular disease, comprising administering a pharmaceutically effective amount of an IL-18 inhibitor, optionally in combination with a pharmaceutically effective amount of an TNF antagonist, to a patient in need thereof.

Having now fully described this invention, it will be appreciated by those skilled in the art that the same can be performed within a wide range of equivalent parameters, concentrations and conditions without departing from the spirit and scope of the invention and without undue experimentation.

While this invention has been described in connection with specific embodiments thereof, it will be understood that it is capable of further modifications. This application is intended to cover any variations, uses or adaptations of the invention following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning an range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

EXAMPLES

Example 1

Inhibition of IL-18 Reduces Peripheral Ischemia

Methods:
Introduction of Hindlimb Ischema

Male C57BL/6J mice (Iffa Creddo, Lyon, France) underwent surgery to induce unilateral hindlimb ischemia. Animals were anesthetized by isoflurane inhalation. The ligature was performed on the right femoral artery, 0.5 cm proximal to the bifurcation of the saphenous and popliteal arteries. Mice (7 animals per group) were then housed under specific pathogen-free conditions for 3 or 28 days. To examine the role of IL-18BP in ischemia-induced angiogenesis, a group of mice was injected with 60 µg of the murine IL-18BP expression plasmid, pcDNA3-mIL18BP in both tibial cranial muscles, as previously described (Mallat et at, 2001). The control mice were injected with the same dosage of the control empty plasmid. Transcutaneous electric pulses (8 square wave electric pulses of 200 V/cm, 20 ms duration at 2 Hz) were delivered by a PS-15 electropulsator (Genetronics) using two stainless steel plate electrodes, placed 4.2 to 5.3 mm apart, at each side of the leg. This strategy was used because it was have previously shown that it increases IL-18BP plasma levels, decreases plasma IL-18 activity and inhibits atherosclerotic plaque development and progression (Mallat et al., 2001).

Quantification of Angiogenesis
Microangiography

Vessel density was evaluated by high definition microangiography at the end of the treatment period, as previously described (Silvestre et at, 2000; Silvestre et al., 2001). Briefly, mice were anesthetized (isoflurane inhalation) and a contrast medium (Barium sulfate, 1 g/ml) was injected through a catheter introduced into the abdominal aorta. Images (3 per animals) acquired by a digital X-ray transducer were assembled in order to obtain a complete view of the hindlimbs. The vessel density was expressed as a percentage of pixels per image occupied by vessels in the quantification area. A quantification zone was delineated by the place of the ligature on the femoral artery, the knee, the edge of the femur and the external limit of the leg.

Capillary Density

Microangiographic analysis was completed by assessment of capillary densities in ischemic and non-ischemic muscles, as previously described (Silvestre et al., 2000; Silvestre et al., 2001). Frozen tissu sections (7 µm) were incubated with rat monoclonal antibody directed against CD31 (20 µg/ml, Pharmingen) to identify capillaries. Immunostains were visualized by using avidin-biotin horseradish peroxydase visualization systems (Vectastain ABC kit elite, Vector Laboratories). Capillary densities were calculated in randomly chosen fields of a definite area, using Histolab software (Microvision).

Laser Doppler Perfusion Imaging

To provide functional evidence for ischemia-induced changes in vascularization, Laser Doppler Perfusion Imaging experiments were performed, as previously described (Silvestre et al., 2000; Silvestre et al., 2001). Briefly, excess hairs were removed by depilatory cream from the limb before imaging, and mice were placed on a heating plate at 37° C. to minimize temperature variation. Nevertheless, to account for variables, including ambient light and temperature, calculated perfusion was expressed as a ratio of ischemic to non-ischemic leg.

Statistical Analysis

Results are expressed as mean±SEM. One way analysis of variance ANOVA was used to compare each parameter. Post hoc Bonferonni's t test comparisons were then performed to identify which group differences account for the significant overall ANOVA. A value of $p<0.05$ was considered as statistically significant.

Results:

Microangiography

Figure 1B:
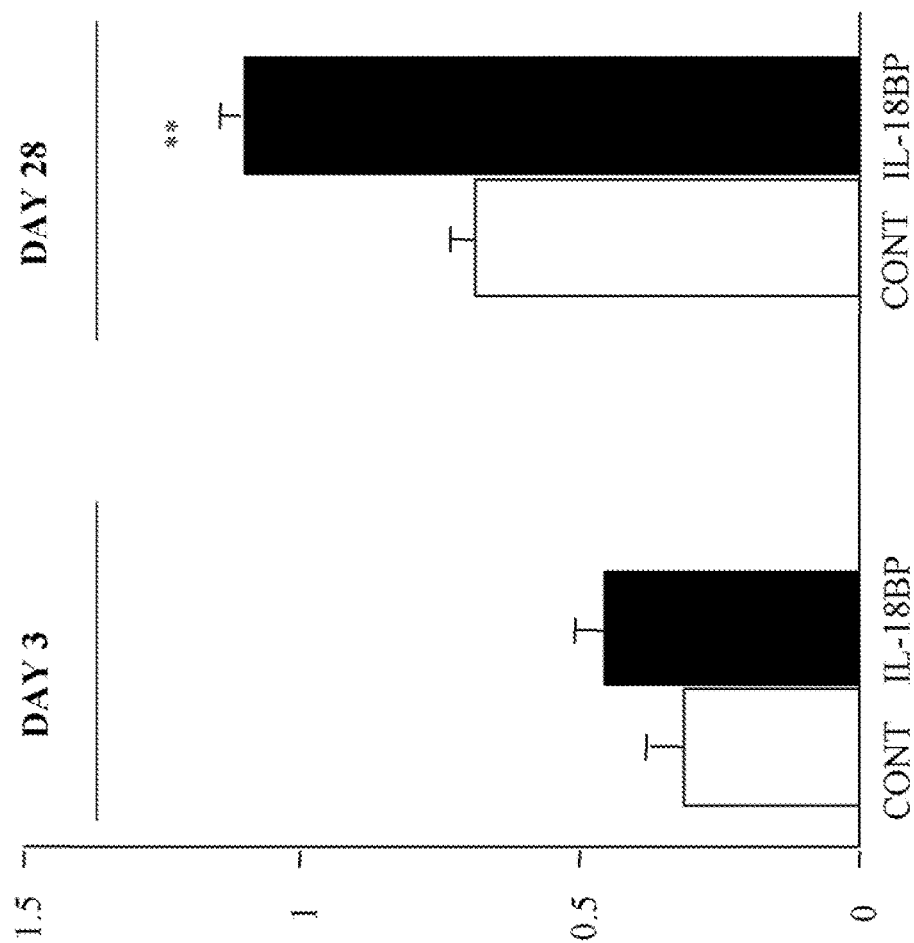

At day 3, ischemic/non-ichemic leg angiographic score ratios were unaffected, in either group (FIG. 1). In contrast, at day 28, angiographic score showed 1.6-fold increase in mice treated with IL-18BP compared to controls ($p<0.01$).

Capillary Density

Microangiographic data were confirmed by capillary density analysis after CD31 staining. At day 28, capillary density of the ischemic leg of control mice was lower than that of the nonischemic leg (415±31 versus 688±42 vessels/$mm^2$, $p<0.01$). However, capillary density of the ischemic leg of IL-18BP-treated mice was significantly higher (1.4-fold increase) than that of control mice (588±48 versus 415±31 vessels/$mm^2$, respectively, $p=0.01$) and did not differ from the level observed in the nonischemic leg.

Laser Doppler Perfusion Imaging

Figure 2A:
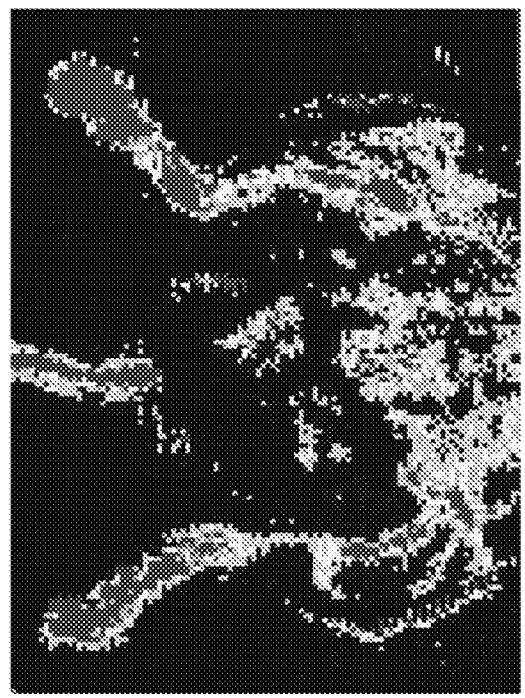
FIG. 2: shows A) Ischemia-induced changes in hindlimb blood flow monitored in vivo by laser Doppler perfusion imaging in mice treated with pcDNA3-mIL18BP (IL-18 BP) or empty plasmid (Control). In color-coded images, normal perfusion is depicted in red, a marked reduction in blood flow of ischemic hindlimb is depicted in blue. B) Quantitative evaluation of blood flow expressed as a ratio of blood flow in ischemic limb to that in non-ischemic one. Values are mean±SEM, n=7 per group. **$p<0.01$ versus control mice.
Figure 2A:
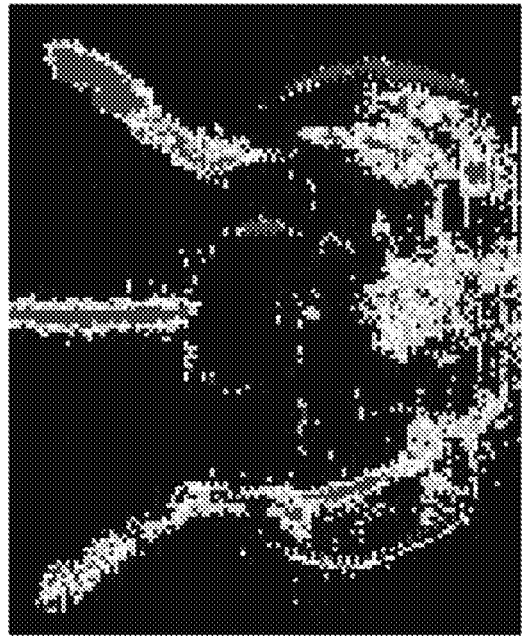
Figure 2B:
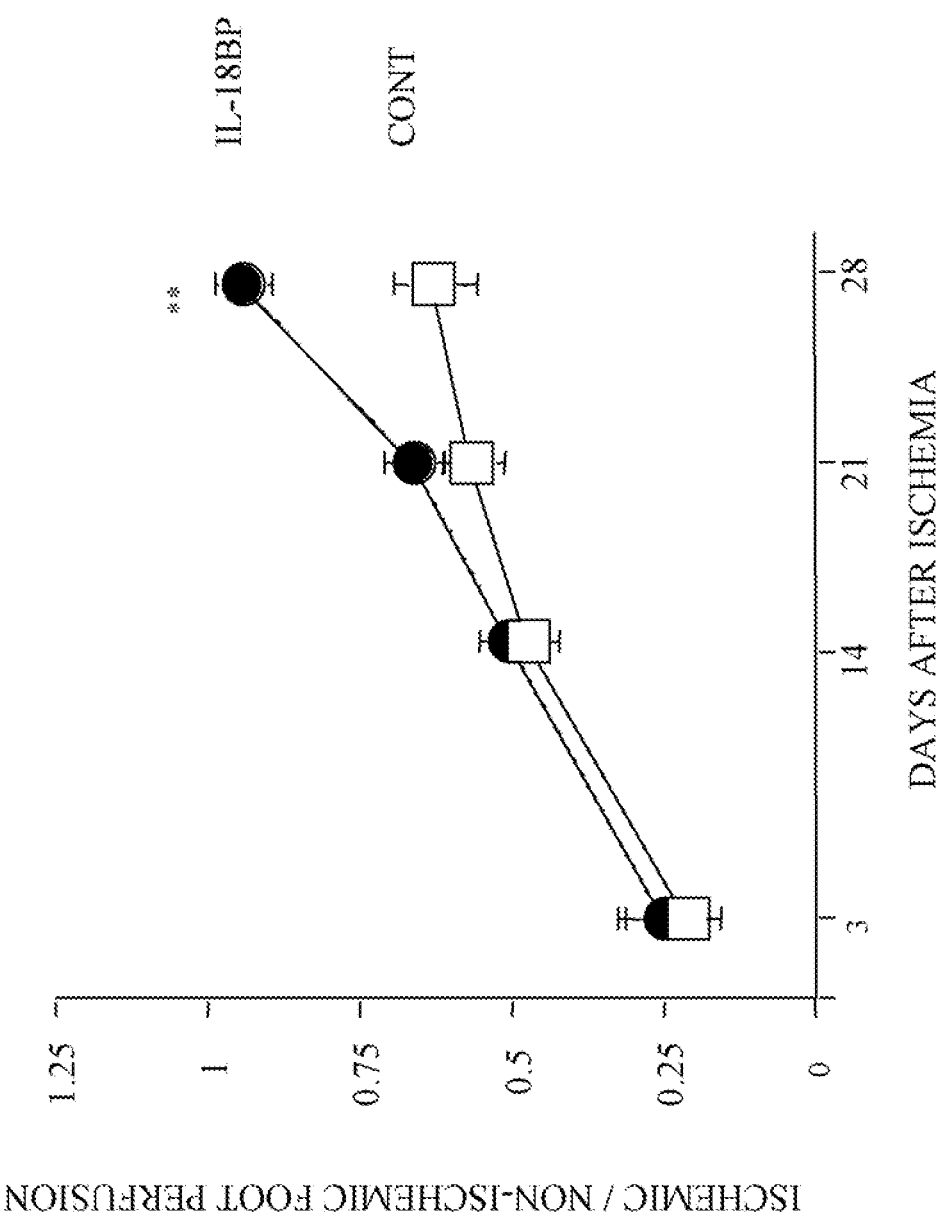

Microangiographic and capillary density measurements were associated with changes in blood perfusion. Hindlimb blood flow recovery occurred in both treated and untreated mice. However, in IL-18BP treated mice, a greater increase in blood flow (foot perfusion) was evident by day 28 compared to control animals (1.5-fold, $p<0.01$, FIG. 2).

Example 2

Regulation of VEGF, Phospho-Akt and eNOS Protein Level

Method:

VEGF, phospho-Akt and eNOS (endothelial nitric oxide synthase protein) expression was determined by western-blot in ischemic and non-ischemic legs, as previously described (Silvestre et al., 2000; Silvestre et al., 2001).

Figure 3A:
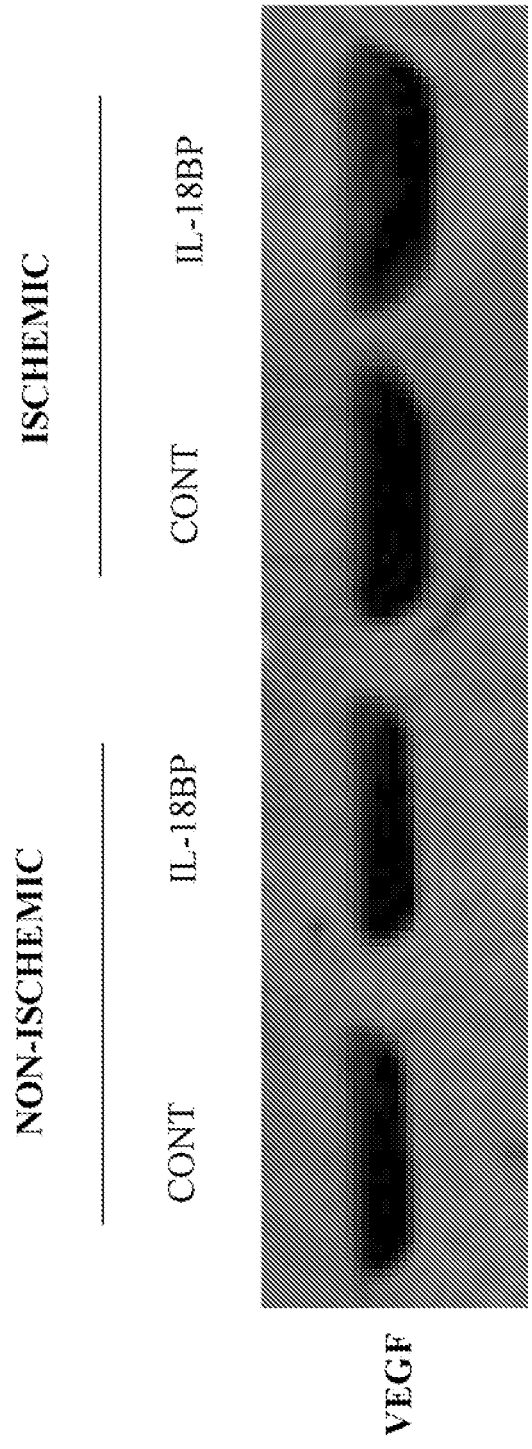
Figure 3C:
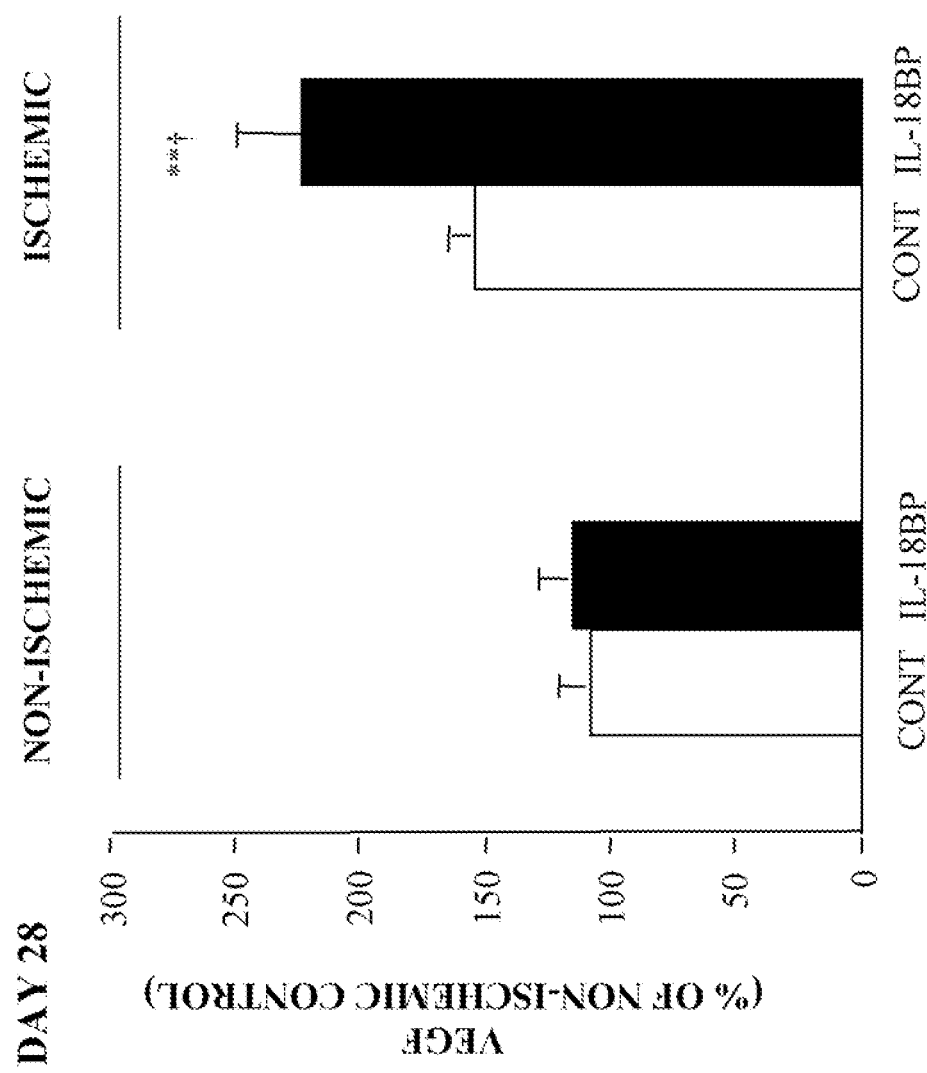

Results:

VEGF. At day 3, no changes in VEGF protein level were observed between the ischemic and non-ischemic legs, in either group. At day 28, in control mice, VEGF protein content tended to increase in the ischemic leg when compared with the non-ischemic one, but this did not reach statistical significance. In contrast, VEGF protein level of the ischemic leg was markedly upregulated by 120% in IL-18BP-treated mice compared to controls ($p<0.05$) (FIG. 3).

Figure 4A:
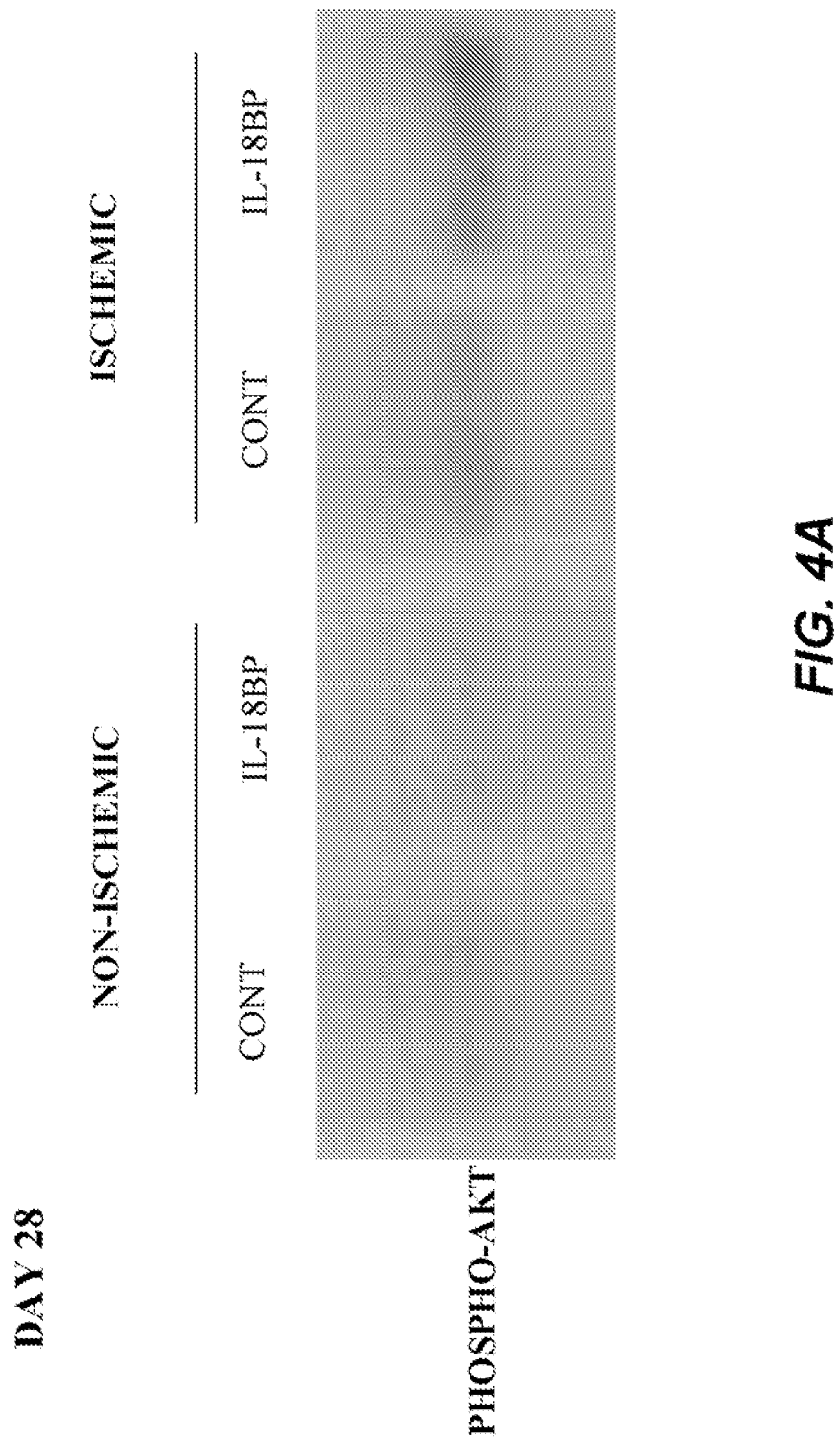
FIGS. 4A-4C show A) Representative western-blot of phospho-Akt protein content in the non-ischemic and ischemic leg, 28 days after femoral artery occlusion. B) and C) Quantitative evaluation of phospho-Akt protein levels expressed as a ratio of protein content in ischemic limb to that in non-ischemic one. Values are mean±SEM, n=7 per group. *$p<0.05$, **$p<0.01$ versus non-ischemic control and †$p<0.05$ versus ischemic control.
Figure 4B:
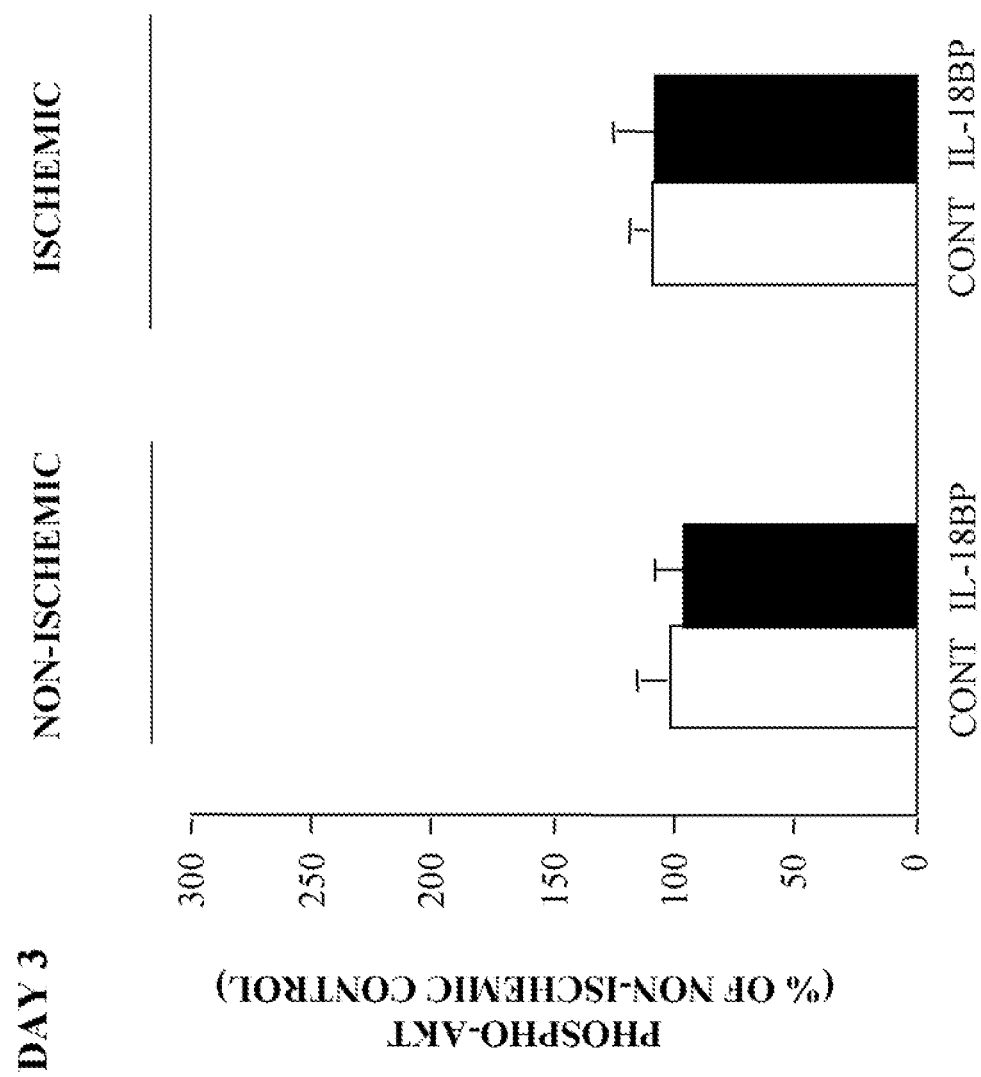
Figure 4C:
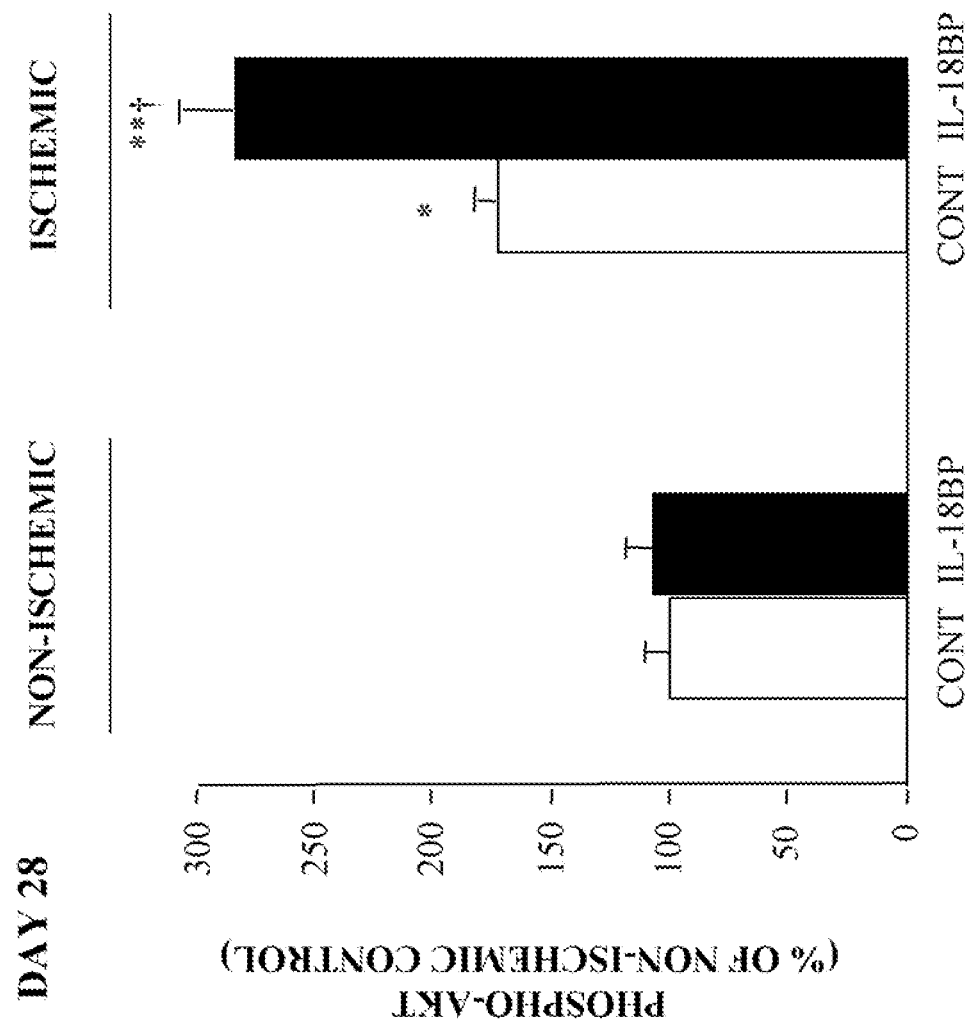
Figure 5A:
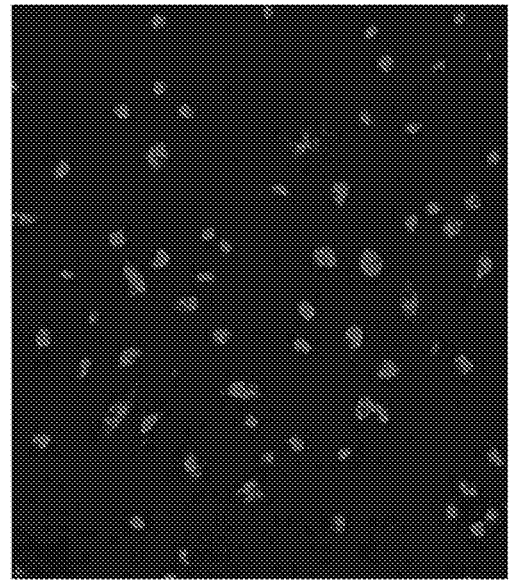
FIGS. 5A-5C show A) Representative images of EPCs (endothelial progenitor cells) isolated from bone marrow of mice without femoral artery ligature (Sham) and of mice treated with pcDNA3-mIL18BP (IL-18BP) or empty plasmid (Control). C) EPCs were characterized as adherent cells with double-positive staining for AcLDL-Dil and von-Willebrand factor (vWF) B) Quantification of double-positive cells in mice treated with pcDNA3-mIL18BP or empty plasmid. Values are mean±SEM, n=5 per group. ***$p<0.001$, versus control mice, ††\$p<0.001$, versus mice without femoral artery ligature (Sham).
Figure 5A:
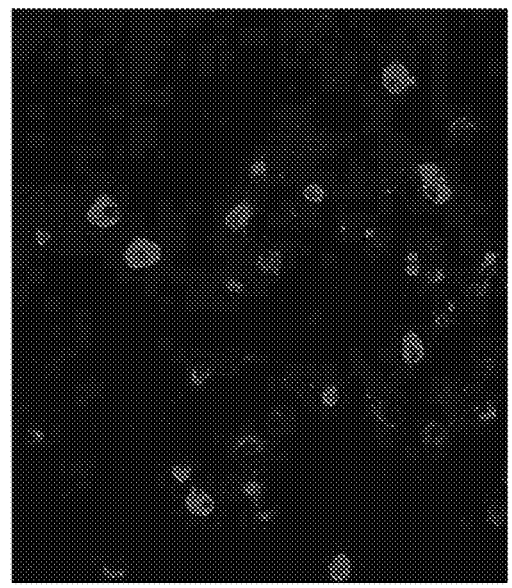
Figure 5B:
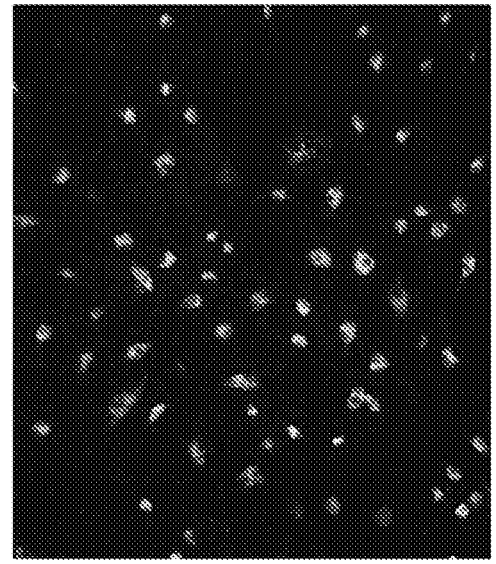
Figure 5B:
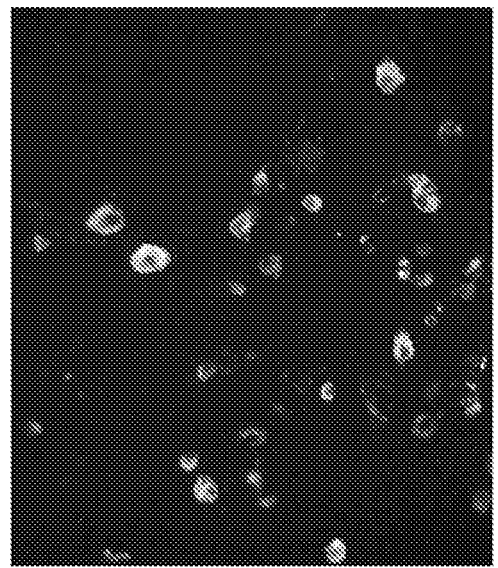
Figure 5C:
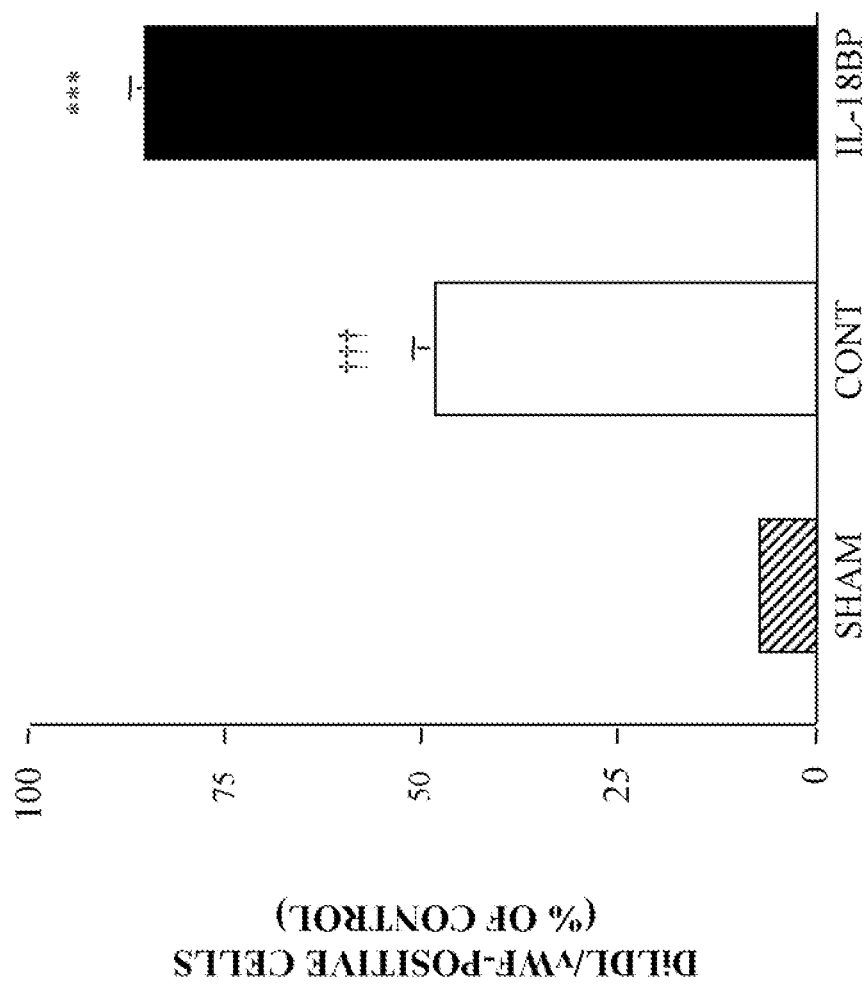

Phospho-Akt. At day 3, phospho-Akt protein level was unchanged in ischemic and non-ischemic hindlimbs whatever the treatment. At day 28, in control mice, phospho-Akt protein content was increased by 60% in ischemic hindlimb over that of non ischemic one ($p<0.01$). This increase in phospho-Akt content of the ischemic leg doubled in mice treated with IL-18BP (110% increase, $p<0.05$ as compared with the increase in the ischemic leg of control mice) (FIG. 4).

eNOS. At day 3, eNOS protein content was unaffected in ischemic (107±8% versus 103±24%) and non ischemic legs (100±12% versus 94±21%) for control and IL-18BP-treated animals, respectively. At day 28, in control mice, eNOS levels were raised by 55% in the ischemic leg in reference to the non-ischemic one (155±8% versus 100±11%, respectively, $p<0.05$). Such an increase was unaffected by IL-18BP treatment (160±12%, $P=0.61$ versus ischemic control).

Example 3

Effect of IL-18BP on EPCs (Endothelial Progenitor Cells)

Methods:

Flow Cytometry Analysis

EPCs cells are thought to derive from Sca-1-positive hematopoietic progenitor cells (Takahashi et al., 1999). The percentage of monuclear cells expressing the EPCs marker protein Sca-1 was then determined by flow cytometry. Seven days after ischemia, mononuclear cells were isolated from peripheral blood (300 µl) and from bone marrow of mice treated with either the empty pcDNA3 plasmid or the pcDNA3-mIL18BP plasmid (n=5 per group). Bone marrow cells were obtained by flushing the tibias and femurs. Low density monuclear cells were isolated by density-gradient centrifugation with Ficoll. Mononuclear cells were then incubated with fluorescein isothiocyanate (FITC) conjugated monoclonal antibodies against Sca-1 (D7, BD Pharmingen). Isotype-identical antibodies served as controls.

EPC Differentiation Assay

Immediately after isolation, $5.10^6$ bone marrow derived monuclear cells were also plated on 35 mm-cell culture dishes coated with rat plasma vitronectin (Sigma) and gelatin (0.1%) and maintained in endothelial basal medium (EBM2, Bio whittaker). After 4 days in culture, nonadherent cells were removed and adherent cells underwent immunochemicals analysis.

To detect the uptake of 1,1'-dioctadecyl-3,3,3',3'-tetramethylindocarbocyanine-labeled acetylated low-density lipoprotein (AcLDL-Dil), cells were incubated with AcLDL-Dil (Tebu) at 37° C. for 1 hour. Cells were then fixed with 2% paraformaldehyde, incubated with a primary polyclonal rabbit antibody directed against and von-Willbrand factor (vWF) (DAKO) for 1 hour, and with FITC-labeled monoclonal antirabbit IgG (H+L) for 30 min (Coulter). Dual-stained cells positive for both AcLDL-Dil and vWF were judged to be EPCs, and they were counted per well. Three independent investigators evaluated the number of EPCs per well by counting three randomly selected high-power fields. Results are then expressed as percentage of total number of mononuclear cells.

Results:

EPCs are thought to derive from Sca-1 positive mononuclear cells (Takahashi et al., 1999). The percentage of Sca-1 positive mononuclear cells in the peripheral blood remained unchanged in IL-18BP-treated mice compared with control animals (31.5±13% versus 28.5±13%, respectively). Similarly, the overall number of Sca-1 positive monuclear cells isolated from bone-marrow did not differ among IL-18BP-treated mice and control animals (4.35±0.95% versus 5.87±0.22%, respectively). Furthermore, IL-18BP treatment did not affect the total number of peripheral blood or bone marrow mononuclear cells (data not shown).

EPCs were isolated and cultivated from bone marrow mononuclear cells and characterized as dual-stained cells positive for AcLDL-Dil and vWF. The percentage of cells with double positive-staining was almost undetectable in non ischemic animals (<5%, n=4). Ischemia induced a marked increase in the percentage of cells with double positive-staining for AcLDL-Dil and vWF (48±3%, p<0.001 versus non ischemic animals). Such an effect was further expanded by IL-18BP treatment (48±3% in controls versus 85±2% in IL-18BP-treated mice, p<0.001) (FIG. 5). Thus, IL-18BP treatment seems to stimulate the differentiation of mononuclear cells into EPCs rather than increase the number of circulating progenitor cells.

REFERENCES

1. Buggemann et al., Eur. J. Immunol. 21:1323-1326 (1991)
2. DiDonato, J A, Hayakawa, M, Rothwarf, D M, Zandi, E. and Karin, M. (1997). Nature 388, 16514-16517.
3. Elliott, M. J., Maini, R. N., Feldmann, M., Long-Fox, A., Charles, P., Bijl, H., and Woody, J. N., 1994, Lancet 344, 1125-1127.
4. Engelmann, H., Novick, D., and Wallach, D., 1990, J. Biol. Chem. 265, 1531-1536.
5. Grantham (1974), Science, 185.862-864.
6. Kim S H, Eisenstein M, Reznikov L, Fantuzzi G, Novick D, Rubinstein M, Dinarello C A. Structural requirements of six naturally occurring isoforms of the IL-18 binding protein to inhibit IL-18. Proc Natl Acad Sci USA 2000; 97:1190-1195.
7. Kim S H et al., J. Immuno. 2001, 166, pp. 148-154.
8. Knight D M, Trinh H, Le J, Siegel S, Shealy D, McDonough M, Scallon B, Moore M A, Vilcek J, Daddona P, et al. Construction and initial characterization of a mouse-human chimeric anti-TNF antibody. Mol Immunol 1993 Nov. 30:16 1443-53
9. Maniatis et al., Molecular Cloning: A Laboratory Manual, Cold Spring Harbor Laboratory, New York, 1982.
10. Meldrum, D. R., Cleveland, J. C., Jr., Cain, B. S., Meng, X. & Harken, A. H. (1998) Ann Thorac Surg 65, 439-43.
11. Mendez, M. M., Green, L. L., Corvalan, J. R. F., Jia X-C., Maynard-Currie, E. E., Yang, X-D., Gallo, M. L., Louie, D. M., Lee, D. V., Erickson, K. L., Luna, J., Roy, C. M-N., Abderrahim, H., Kirshenbaum, F., Noguchi, M., Smith, D. M., Fukushima, A., Hales, J. F., Finer, M. H., Davis, C. G., Zsebo, K. M. and Jakobovits, A. (1997). "Functional transplant of megabase human immunoglobulin loci recapitulates human antibody response in mice". Nature Genetics, 15, 146-56.
12. Nakamura, K, Okamura, H, Nagata, K. and Tamura, T. (1989). Infect. Immun. 57, 590-595.
13. Novick, D, Kim, S-H, Fantuzzi, G, Reznikov, L, Dinarello, C, and Rubinstein, M (1999). Immunity 10, 127-136.
14. Parnet, P, Garka, K E, Bonnert, T P, Dower, S K, and Sims, J E. (1996), J. Biol. Chem. 271, 3967-3970.
15. Silvestre, J. S., Mallat Z, Duriez M, Tamarat R, Bureau M F, Scherman D, Duverger N, Branellec D, Tedgui A, Levy B I. 2000. Antiangiogenic effect of interleukin-10 in ischemia-induced angiogenesis in mice hindlimb. Circ. Res. 87: 448-452.
16. Silvestre, J. S., Mallat Z, Tamarat R, Duriez M, Tedgui A and Levy B I. 2001. Regulation of Matrix Metalloproteinase activity in ischemic tissue by interleukin-10: Role in ischemia-induced angiogenesis. Circ. Res. 89: 259-264.
17. Takahashi, T., Kalka, C., Masuda, H., Chen, D., Silver, M., Kearney, M., Magner, M., Isner, J. M., Asahara, T. 1999. Ischemia- and cytokine-induced mobilization of bone marrow-derived endothelial progenitor cells for neovascularization. Nat. Med. 5:434-438.
18. Torigoe, K., Ushio, S., Okura, T., Kobayashi, S., Taniai, M., Kunikate, T., Murakami, T., Sanou, O., Kojima, H., Fuji, M., Ohta, T., Ikeda, M., Ikegami, H. & Kurimoto, M. (1997) J Biol Chem272, 25737-25742.
19. Tomizuka et al., Proc. Natl. Acad. Sci. USA 97:722-727 (2000)
20. Tucci, A., James, H., Chicheportiche, R., Bonnefoy, J. Y., Dayer, J. M., and Zubler, R. H., 1992, J. Immunol. 148, 2778-2784.
21. Yoshimoto T, Takeda, K, Tanaka, T, Ohkusu, K, Kashiwamura, S, Okamura, H, Akira, S and Nakanishi, K (1998). J. Immunol. 161, 3400-3407.

The invention claimed is:

1. A method for stimulating neovascularization in an individual having symptoms of gangrene and/or ulcer of the limb resulted from limb ischemia the method comprising administering to the individual having symptoms of gangrene and/or ulcer an effective tissue perfusion increasing amount of a composition comprising an IL-18 binding protein and a pharmaceutically acceptable carrier.

2. The method of claim 1 further comprising a step of detecting an individual having symptoms of gangrene and/or ulcer of the limb resulted from limb ischemia prior to administering the IL-18 binding protein to the individual.

3. The method of claim 2, wherein the step of detecting the individual having symptoms of gangrene and/or ulcer of the limb resulted from limb ischemia comprises detecting decreased blood flow and pressure in toes, feet or fingers of the individual.

4. The method according to claim 1, wherein the IL-18 binding protein is glycosylated at least at one site.

5. The method according to claim 1, wherein the IL-18 binding protein is PEGylated.

6. The method according to claim 1, wherein the IL-18 binding protein is fused to an immunoglobulin (Ig) moiety.

* * * * *